(12) United States Patent
Dolle, III et al.

(10) Patent No.: US 6,255,120 B1
(45) Date of Patent: Jul. 3, 2001

(54) COMBINATORIAL LIBRARY OF SUBSTITUTED STATINE ESTERS AND AMIDES VIA A NOVEL ACID-CATALYZED REARRANGEMENT

(75) Inventors: Roland Ellwood Dolle, III, King of Prussia, PA (US); Cullen Lee Cavallaro, Hightstown; Timothee Felix Herpin, Princeton, both of NJ (US)

(73) Assignee: Pharmacopeia, Inc., Princeton, NJ (US)

( * ) Notice: Subject to any disclaimer, the term of this patent is extended or adjusted under 35 U.S.C. 154(b) by 0 days.

(21) Appl. No.: 09/079,932

(22) Filed: May 15, 1998

Related U.S. Application Data

(63) Continuation of application No. 08/843,214, filed on Apr. 14, 1997.
(51) Int. Cl.[7] .......................... G01N 33/543; G01N 33/53
(52) U.S. Cl. .......................... 436/518; 436/523; 436/524; 435/7.1; 435/DIG. 1; 435/DIG. 22; 435/DIG. 34; 435/DIG. 35; 544/390; 544/400; 564/193; 546/343; 546/348
(58) Field of Search .............................. 435/7.1, DIG. 1, 435/22, 34, 35; 436/518, 523, 524; 544/390, 400; 564/193; 546/343, 348

(56) References Cited

U.S. PATENT DOCUMENTS

| | | |
|---|---|---|
| 5,565,324 | * 10/1996 | Still et al. . |
| 5,734,054 | * 3/1998 | Dolle et al. . |
| 5,872,262 | * 2/1999 | Dolle et al. . |
| 5,892,038 | * 4/1999 | Dolle et al. . |
| 5,972,719 | * 10/1999 | Dolle et al. ..................... 436/518 |
| 5,976,894 | * 11/1999 | Dolle et al. ..................... 436/501 |

OTHER PUBLICATIONS

Dolle, Molecular Diversity, vol. 2, No. 4, 223–236, 1997.*
Gordon and Gallop, Journal of Med. Chem., vol. 37, No. 10, 1385–1401, 1994.*
Silva et al., PNAS USA, vol. 93, 10034–10039, Sep. 1996.*
Agarwal et al., J. Med. Chem., vol. 29, 2519–2524, 1986.*

* cited by examiner

*Primary Examiner*—Bennett Celsa
(74) *Attorney, Agent, or Firm*—Heslin & Rothenberg, P.C.

(57) ABSTRACT

A combinatorial chemical library comprising a plurality of members of the Formula [S]—C(O)—L'-Z containing hydroxyamides is disclosed, in which [S] represents a solid support and L'-Z is a linker/compound residue. In this library, Z is

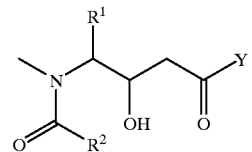

and Y is —$NR^3R^4$ or —$OR^9$. $R^3$ and $R^4$ are independently selected from the group consisting of H, alkyl, aralkyl, heteroarylalkyl, heterocycloalkyl, —$CH(R^5)CH(R^6)OH$, —$CH(R^5)C(O)NHR^6$ and —$CH(R^5)C(O)NHCH(R^6)C(O)NHR^7$. $R^3$ and $R^4$ together are

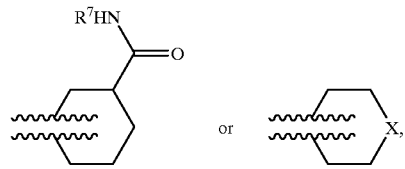

wherein X=O or $NR^8$ and $R^9$ is aryl, aralkyl or $R^7CH\!=\!CH(CH_2)_n$. The combinatorial library can be optionally encoded with identifiers T'-L, which are covalently attached to the solid support. The methods of synthesizing such a library are described. The use of such library in assays to discover biologically active compounds is also disclosed.

17 Claims, No Drawings

COMBINATORIAL LIBRARY OF SUBSTITUTED STATINE ESTERS AND AMIDES VIA A NOVEL ACID-CATALYZED REARRANGEMENT

CROSS-REFERENCE

This appln is a cont of Ser. No. 08/843,214 filed Apr. 14, 1997.

Combinatorial Amide Alcohol Libraries, U.S. Ser. No. 08/843,214, filed Apr. 14, 1997, is incorporated herein by reference. Combinatorial Hydroxy-Amino Acid Amide Libraries, U.S. Ser. No. 08/743,960, filed Nov. 5, 1996, is incorporated herein by reference.

All patents and other references cited herein are incorporated by reference.

FIELD OF THE INVENTION

This invention relates generally to the synthesis of chemical compounds, and more particularly, to the synthesis of a combinatorial library of hydroxyamides.

BACKGROUND OF THE INVENTION

Methods for the synthesis of large numbers of diverse compounds that can be screened for various possible physiological or other activities are advantageous (Ellman, et al. *Chem. Rev.* 96, 555–600 (1996)). Techniques have been developed in which individual units are added sequentially as part of the chemical synthesis to produce all, or a substantial number, of the possible compounds which can result from all the different choices possible at each sequential stage of the synthesis. Many diverse compounds are produced by a series of reactions of a multiplicity of synthons in various combinations. Each compound in a combinatorial library results from the reaction of a subset of synthons. For these techniques to be successful, the compounds should be amenable to methods by which one can determine the structure of the compounds so made. A premier example of such techniques is the production of oligonucleotide "tags" in parallel with oligopeptide compounds of interest (Brenner and Lerner *Proc. Natl. Acad. Sci. USA* 81, 5381–83 (1992) and WO 93/20242). Methods for particle-based synthesis of random oligomers wherein identification tags on the particles are used to facilitate identification of the synthesized oligomer sequence are known (WO 93/06121). A detachable tagging system that is useful in sequential synthesis of large numbers of compounds has been disclosed (Ohlmeyer et al., *Proc. Natl. Acad. Sci. USA*, 90, 10922–10926 (1993)).

SUMMARY OF THE INVENTION

The present invention relates to a combinatorial library of hydroxyamides optionally encoded with tags. The present invention also relates to the use of this library in assays to discover biologically active compounds.

In one aspect, the invention relates to a combinatorial chemical library for biological assay comprising a plurality of members of Formula I:

$$(T-L)_q-[S]-C(O)-L'-Z \qquad I$$

wherein:

T is a tag;

L is a first linker;

T-L- together form an identifier residue;

q is 0–30;

[S] is a solid support;

-L' is a second linker;

-Z is a compound of formula:

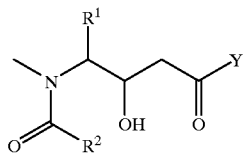

wherein:

$R^1$ is chosen from the group consisting of alkyl, aralkyl, aryl, —$(CH_2)_n$—NHC(O)$R^5$ and —$(CH_2)_n$-cycloalkyl; where n=1–4;

$R^2$ is chosen from the group consisting of alkyl, aralkyl, aryl, aryloxyalkyl, cycloalkyl, —$(CH_2)_n$-cycloalkyl, heteroaryl, —CH($R^6$)OC(O)NH$R^5$,

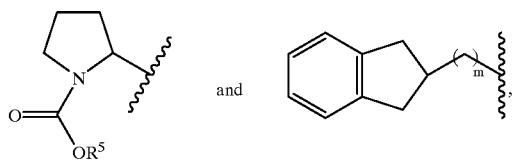

wherein m=0–3; or $R^2$ is the descarboxy residue of an N-capped-α-amino acid;

Y is —$NR^3R^4$ or —$OR^9$;

$R^3$ and $R^4$ are independently selected from the group consisting of H, alkyl, aralkyl, heteroarylalkyl, heterocycloalkyl, —CH($R^5$)CH($R^6$)OH, —CH($R^5$)C(O)NH$R^6$ and —CH($R^5$)C(O)NHCH($R^6$)C(O)NH$R^7$; or $R^3$ and $R^4$ together are

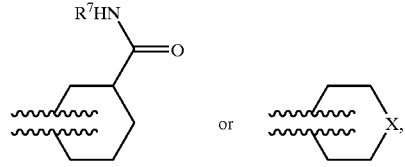

wherein X=O or $NR^8$;

$R^5$ are independently selected from the group consisting of alkyl, aralkyl and aryl;

$R^6$ is H, lower alkyl, aryl or aralkyl;

$R^7$ is H or alkyl;

$R^8$ is chosen from the group consisting of H, $R^5$, C(O)$R^5$, C(O)O$R^5$ and —$SO_2R^5$; and $R^9$ is alkyl, aryl, aralkyl or $R^7CH=CH(CH_2)_{\overline{n}}$.

The invention further relates to methods of synthesizing a library comprising a plurality of members of Formula I.

Another aspect of the invention is the use of the herein described combinatorial library in assays to discover biologically active compounds of Formula III:

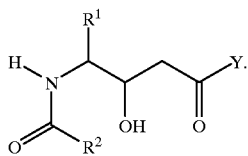

III

Thus, another aspect of the invention is a method for identifying a compound having a desired characteristic, which comprises testing a combinatorial library comprising a plurality of members of Formula I, either attached to or detached from the solid supports, in a biological assay which identifies compounds of Formula III having the desired characteristics.

DETAILED DESCRIPTION OF THE INVENTION

Abbreviations and Definitions

The following abbreviations and terms have the indicated meanings throughout:
Ac=acetyl
AFC=7-aminotrifluoromethyl coumarin
allyl=—CH$_2$CH=CH$_2$
AMC=7-amino-4-methyl coumarin
ANP=atrial natriuretic peptide
BNB=4-bromomethyl-3-nitrobenzoic acid
BSA=bovine serum albumin
BOC=t-butyloxy carbonyl
Bu=butyl
c—=cyclo
CCD=charge-coupled device
Cdk-4=Cyclin-dependent kinase-4
DABCYL=4-(4-dimethylaminophenylazo)benzoic acid
Dansyl=5-(dimethylamino)-1-naphthalenesulfonyl
DBU=Diazabicyclo[5,4,0]undec-7-ene
DCM=Dichloromethane=methylene chloride=CH$_2$Cl$_2$
DIC=diisopropylcarbodiimide
DIEA=diisopropylethyl amine
DMAP=4-N,N-dimethylaminopyridine
DMF=N,N-dimethylformamide
DMSO=Dimethyl sulfoxide
DNA=deoxyribonucleic acid
DVB=1,4-divinylbenzene
EDANS=5-[(2-aminoethyl)amino]naphthalene-1-sulfonic acid
EtOAc=Ethyl acetate
FACS=fluorescence activated cell sorting
Fmoc=9-fluorenylmethoxycarbonyl
GC=gas chromatography
HFC=4-trifluoromethylumbelliferyl
HIV=Human immunodeficiency virus
HOAc=acetic acid
HOBt=hydroxybenzotriazole
hr=hour(s)
IBX=iodoxybenzoic acid
IL=interleukin
in vacuo=under vacuum
m—=meta
MAP=microtubule-associated proteins
Me=methyl
MeOH=methanol
MNA=4-methoxy-2-naphthylamine
NAD=nicotinamide adenine dinucleotide
NADH=nicotinamide adenine dinucleotide, reduced form
NADP=nicotinamide adenine dinucleotide phosphate
NADPH=nicotinamide adenine dinucleotide phosphate, reduced form
NBD=7-nitrobenz-2-oxa-1,3-diazol-4-yl
PEG=polyethylene glycol
PfP=pentafluorophenyl
Ph=phenyl
PhOH=phenol
PKA=Protein kinase A
pyr=pyridine
RNA=Ribonucleic acid
r.t.=room temperature
SAR=structure activity relationship
sat'd=saturated
s—=secondary
SPA™=scintillation proximity assay
t—=tertiary
TBS=tert-butyldimethylsilyl
TEA=triethylamine
TFA=trifluoroacetic acid
THF=tetrahydrofuran
TMS=trimethylsilyl
Tris=tris(hydroxymethyl)aminomethane
Tween 20=polyoxyethylenesorbitan monolaurate
U=unit
UV=ultraviolet light
v=volume
wt=weight "Acylamino" means acylamino groups of from 1 to 8 carbon atoms of a straight, branched or cyclic configuration and combinations thereof. Examples of acylamino groups include: acetylamino, butyrylamino, cyclohexylcarbonylamino, and the like.

"Alkenyl" is $C_2$–$C_8$ alkenyl group of a linear, branched, or cyclic ($C_5$–$C_6$) configuration and combinations thereof. Examples of alkenyl groups include: vinyl, allyl, isopropenyl, pentenyl, hexenyl, c-hexenyl, 1-propenyl, 2-butenyl, 2-methyl-2-butenyl, and the like.

"Alkoxy" means alkoxy groups of from 1 to 8 carbon atoms of a straight, branched, cyclic configuration and combinations thereof. Examples of alkoxy groups include: methoxy, ethoxy, propoxy, isopropoxy, cyclopropyloxy, cyclohexyloxy and the like.

"Alkyl" is intended to include linear or branched hydrocarbon structures and combinations thereof.

"Aralkyl" means an alkyl containing an aryl ring. For example: benzyl, phenethyl, 4-chlorobenzyl, 2,2-diphenylethyl and the like.

"Aryl" is a 6-membered or 10-membered aromatic ring system where each of the rings is optionally substituted with 1–3 substituents selected from alkyl, halogen, hydroxy, alkoxy, aryloxy, haloalkyl, phenyl and heteroaryl; and wherein the phenyl ring is optionally substituted with 1–3 substituents selected from alkyl, halogen or alkoxy. Examples of aryl groups are phenyl, 3,4-dichlorophenyl, biphenyl and naphthyl.

"Aryloxy" means a phenoxy or naphthyloxy group where the phenyl or naphthyl ring is optionally substituted with 1 to 2 groups selected from halo, alkoxy or alkyl.

"Aryloxyalkyl" means an alkyl containing a phenoxy or naphthyloxy group.

"Carboxyalkyl" means —C(O)R where R is alkyl.

"Cycloalkyl" includes cycloalkyl groups of from 3 to 12 carbon atoms. Examples of "cycloalkyl" groups include: c-propyl, c-butyl, c-pentyl, c-hexyl, 2-methylcyclopropyl, norbornyl, adamantyl and the like.

"Haloalkyl" means one or more hydrogen atoms present in an alkyl group are replaced with a halogen atom, except for the methylene hydrogens adjacent to the oxygen atom. For example: trifluoromethyl, 2-chloroethyl and 2,2,2-trifluoroethyl.

Halogen includes F, Cl, Br and I, with F and Cl as the preferred groups.

"Heteroaryl" means a 5- or 6-membered heteroaromatic ring containing 1–4 heteroatoms selected from O, N and S; or a bicyclic 9- or 10-membered heteroaromatic ring system containing 1–4 heteroatoms selected from O, N and S; where the methine H atoms may be optionally substituted with alkyl, alkoxy or halogen. The 5- to 10-membered aromatic heterocyclic rings include: imidazole, pyridine, indole, thiophene, benzopyranone, thiazole, furan, benzimidazole, quinoline, isoquinoline, quinoxaline, pyrimidine, pyrazine, tetrazole, pyrazole and the like.

"Heteroaralkyl" means an alkyl containing a heteroaryl ring. For example: pyridinylmethyl, pyrimidinylethyl and the like.

"Heterocycloalkyl" means a 5- or 6-membered heterocyclic ring containing 1–2 heteroatoms selected from O, N, and S; or a bicyclic 9- or 10-membered heterocyclic ring system containing 1–3 heteroatoms selected from O, N and S; where the methylene atoms may be optionally substituted with alkyl, alkoxy, —C(O)NH$_2$, carboxyalkyl or halogen and N atoms may be optionally substituted with alkyl, aralkyl, or carboxyalkyl. Examples of 5- to 10-membered heterocycloalkyl rings include: decahydroquinolinyl, morpholinyl, piperazinyl, piperidinyl, pyrrolidinyl, tetrahydrofuranyl, tetrahydropyranyl, tetrahydrothiophenyl and the like.

"Lower Alkyl" means alkyl groups of from 1 to 12 carbon atoms. Examples of alkyl groups include: methyl, ethyl, propyl, isopropyl, butyl, s-and t-butyl, pentyl, hexyl, octyl and the like.

The "Descarboxy residue" of an N-protected-α-amino acid refers to a substituent that, together with the carbonyl to which it is attached, represents an α-amino acid in which the basicity of the amino functionality has been masked by an acyl group or carbamate capping group. Such groups are well known to persons of skill in the art and include: acetyl (Ac), butyryl, benzyloxycarbonyl (CBZ) and the like. Preferred α-amino acids are the naturally occurring amino acids and their commercially available analogs (e.g. alanine, leucine, etc.)

For the purpose of the present invention, the term "combinatorial library" means a collection of molecules based upon a logical design and involving the selective combination of building blocks by means of simultaneous chemical reactions. Each species of molecules in the library is referred to as a member of the library. The combinatorial library of the present invention represents a collection of molecules of sufficient number and diversity of design to afford a rich molecular population from which to identify biologically active members.

For the purpose of the present invention, "residue" shall mean the portion of the reagent that is incorporated into the product molecule resulting from the reaction between the reagent and the molecule designated as the starting material. For examples, the residues (NHCH(R$^1$)CH$_2$OTBS) of amino alcohols (H$_2$NCH(R$^1$)CH$_2$OTBS) are shown in Table 2-1; residues (R$^2$C(O)) of carboxylic acids (R$^2$CO$_2$H) in Table 2-2; residues (R$^4$R$^3$N) of amines (R$^4$R$^3$NH) in Table 2-4; and residues (CHCO$_2$R$^9$) of Wittig esters (Ph$_3$PCHCO$_2$R$^9$) in Table 2-5.

"Independently selected" means two substituents in the same structure having the same definition whereby the two substituents may be the same or different.

For the present invention, R$^1$ chosen from the "amino alcohol residues" shall mean R$^1$ chosen from those residues as shown in Table 2-1. Examples of the substituents of "amino alcohol residues" are R$^1$ as alkyl, aralkyl, aryl, —(CH$_2$)$_n$—NHC(O)R$^5$ and —(CH$_2$)$_n$-cycloalkyl; where n=1–4 as substituents on amino alcohols. Specific examples are 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl and 4-phenylbenzyl as substituents on amino alcohols.

For the present invention, R$^2$ chosen from the "carboxylic acid residues" shall mean R$^2$ chosen from those residues as shown in Table 2-2. Examples of the substituents of "carboxylic acid residues" are R$^2$ as alkyl, aralkyl, aryl, aryloxyalkyl, cycloalkyl, —(CH$_2$)$_n$-cycloalkyl, heteroaryl, —CH(R$^6$)OC(O)NHR$^5$,

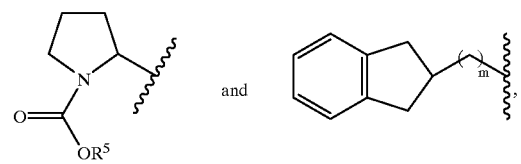

wherein m=0–3; or R$^2$ as the descarboxy residue of an N-capped-α-amino acid. Specific examples are (N-benzyloxycarbonyl)pyrrolidin-2-yl, 4-butoxyphenyl, 4-chlorophenoxymethyl, cyclohexyl, 2-cyclopentylethyl, cyclopropyl, 3,4-dichlorophenyl, 2,3-difluorophenyl, 2,4-dimethoxyphenyl, 3-(3,4-dimethoxyphenyl)propyl, 2,6-dimethylphenoxymethyl, 2,2-dimethylpropyl, 2,2-diphenylethyl, 2-fluoro-4-trifluoromethylphenyl, 2-furanyl, indan-2-ylmethyl, 4-(2-methoxy)ethoxyphenethyl, 3-methylbutyl, 1-naphthyl, 2-naphthyloxymethyl, pentyl, 4-phenoxyphenyl, phenyl, 4-(phenyl)phenyl, 3-phenylpropyl, 3-pyridinyl, 3-quinolinyl and the following residues:

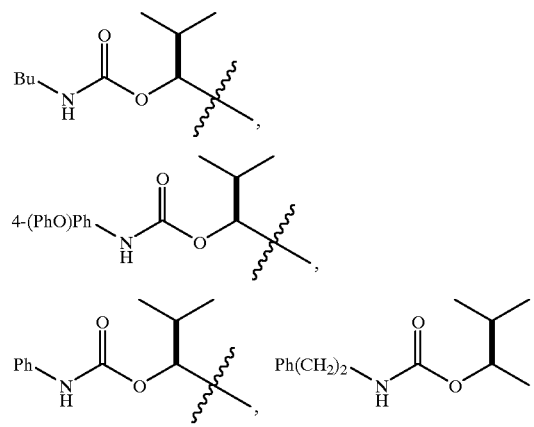

as substituents on carboxylic acids.

For the present invention, R$^3$ and R$^4$ chosen from the "amine residues" shall mean R$^3$ and R$^4$ chosen from those residues as shown in Table 2-4. Examples of the substituents of "amine residues" are R$^3$ and R$^4$ as H, alkyl, aralkyl, heteroarylalkyl, heterocycloalkyl, —CH(R$^5$)CH(R$^6$)OH, —CH(R$^5$)C(O)NHR$^6$ and —CH(R$^5$)C(O)NHCH(R$^6$)C(O)NHR$^7$; or R$^3$ and R$^4$ together are wherein X=O or NR[8] as substituents on amines. R[5] is alkyl, aralkyl or aryl. R[6] is H, lower alkyl, aryl or aralkyl. R[7] is H or alkyl. R[8] is chosen from the group consisting of H, R[5], C(O)R[5], C(O)OR[5] and —SO$_2$R[5]. Specific examples of R[3] and R[4] are hydrogen, 2-benzamidazolylmethyl, N-benzylpiperidin-4-yl, N-benzylpyrrolidin-3-yl, butyl, 3-imidazolylprop-1-yl, 3-phenylhydroxyprop-2-yl, 1,2-diphenylhydroxyeth-2-yl, or R[3] and R[4] together are 3-carboxamidopiperidinyl or 4-methylpiperazinyl as substituents on amines. Specific examples of R[5] are benzyl, butyl, methyl, phenethyl, phenoxyphenyl and phenyl. Specific examples of R[6] are benzyl, butyl, hydrogen, isobutyl and phenyl. Specific examples of R[7] are hydrogen, ethyl, methyl, isopropyl, butyl and pentyl; and specific examples of R[8] are methyl and ethyl.

For the present invention, R[9] chosen from the "Wittig ester residues" shall mean R[9] chosen from those residues as shown in Table 2-5. R[9] is alkyl, aryl, aralkyl or R$_7$CH=CH(CH$_2$)$_{\overline{n}}$. Examples of the substituents of "Wittig ester residues" are R[9] as ethyl, allyl, propyl, butyl and benzyl.

In the present invention, the "reagent" shall mean the chemical entity shown in the reaction scheme or named and described in the specification. The reagent is reacted with the molecule designated as the starting material. For example, reagents are the amino alcohols and carboxylic acid chlorides shown in Scheme 1 and the Wittig esters and amines in Scheme 2.

For the present invention, alcohol solvents mean C$_{1-4}$ linear or branched alkylhydroxy solvents. Examples include: methanol, ethanol, isopropanol and other such alcohols well know in the art.

In the present invention, dilute acid solution means alcohol solvents as described above, containing 1–5% organic or inorganic acids such as acetic acid, hydrochloric acid, sulfuric acid, trifluoroacetic acid and other such acids well know in the art.

For the present invention, mild oxidizing agents include the following reagents: iodoxybenzoic acid; 1,1-triacetoxy-1,1-dihydro-1,2-benziodoxol-3-(1H)-one; and other such oxidizing agents well known in the art.

In the present invention, anhydrous solvents are organic solvents containing 1% or less water by volume.

In the present invention, a base as a reagent shall include: pyridine, piperidine, triethylamine, DBU and other well known organic bases.

I. Preferred Embodiments

In one aspect, the invention relates to a combinatorial chemical library for biological assay comprising a plurality of members of the Formula I:

$$(T'-L)_q-[S]-C(O)-L'-Z \qquad I$$

wherein:
T' is a tag;
L is a first linker;
T'-L- together form an identifier residue;
q is 0–30;
[S] is a solid support;
-L' is a second linker;
-Z is a compound of formula:

wherein:
R[1] is chosen from the group consisting of alkyl, aralkyl, aryl, —(CH$_2$)$_n$—NHC(O)R[5] and —(CH$_2$)$_n$-cycloalkyl; where n=1–4;
R[2] is chosen from the group consisting of alkyl, aralkyl, aryl, aryloxyalkyl, cycloalkyl, —(CH$_2$)$_n$-cycloalkyl, heteroaryl, —CH(R[6])OC(O)NHR[5], wherein m=0–3; or R[2] is the descarboxy residue of an N-capped-α-amino acid;
Y is —NR[3]R[4] or —OR[9];
R[3] and R[4] are independently selected from the group consisting of H, alkyl, aralkyl, heteroarylalkyl, heterocycloalkyl, —CH(R[5])CH(R[6])OH, —CH(R[5])C(O)NHR[6] and —CH(R[5])C(O)NHCH(R[6])C(O)NHR[7]; or
R[3] and R[4] together are wherein X=O or NR[8];
R[5] are independently selected from the group consisting of alkyl, aralkyl or aryl;
R[6] is H, lower alkyl, aryl or aralkyl;
R[7] is H or alkyl;
R[8] is chosen from the group consisting of H, R[5], C(O)R[5], C(O)OR[5] and —SO$_2$R[5]; and $R^9$ is alkyl, aryl, aralkyl or $R^7CH=CH(CH_2)_{\overline{n}}$.

Preferred libraries of Formula I are those wherein T'-L- is of the Formula II

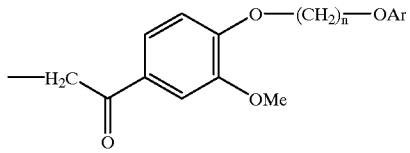

wherein:

n=3–12;

Ar is halophenyl; and q=3–12.

More preferred libraries of Formula I are those wherein T'-L- is of the Formula II and n is 3–12 and Ar is a pentachlorophenyl or n is 3–6 and Ar is 2,4,6-trichlorophenyl.

Other preferred libraries of Formula I are those wherein -L'- is

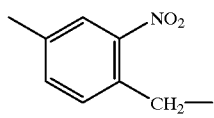

(a)

such that the left-hand bond shown is the point of attachment to —C(O)— and the methylene bond is the point of attachment to -Z.

When q is zero, the resultant untagged libraries are of Formula I':

[S]—C(O)—L'-Z    I' wherein the symbols are as defined for Formula I.

Another preferred embodiment of the invention is a combinatorial library comprising a plurality of members of Formula I wherein:

-L' is chosen from the group consisting of the eight members of Table I.

Yet another preferred embodiment of the invention is a combinatorial library comprising a plurality of members of Formula I wherein:

-L' is a photocleavable linker.

Depending on the choice of L' (see Table 1), the compounds or ligands, -Z, of Formula I may be detached by photolytic, oxidative, basic or other cleavage techniques. For example, when -L'- is a residue of formula (a), photolytic cleavage may be represented by:

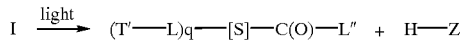

wherein L" is the residue from L' and the genus H-Z may be represented by Formula III:

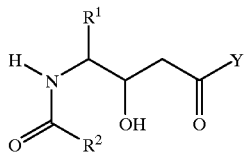

III

A preferred embodiment of the invention is the use of amino-functionalized polyethylene glycol-grafted resin, shown as [S] in Formula I. [S], as defined, is shown as

in the schemes for simplicity.

Another preferred embodiment of the invention is a library comprising a plurality of members of Formula IV:

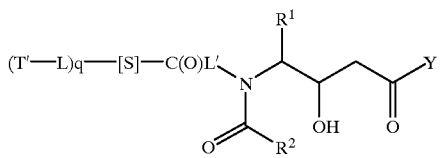

IV wherein:

Y is —$NR^3R^4$.

Yet another preferred embodiment of the invention is a library comprising a plurality of members of Formula IV:

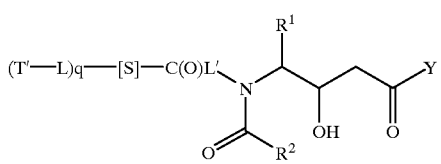

IV wherein:

Y is —$OR^9$.

Another preferred embodiment of the invention is a library comprising a plurality of members of Formula IV:

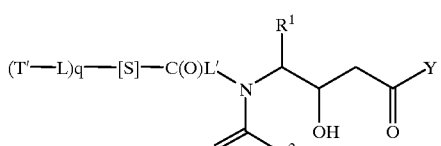

IV wherein:

$R^1$ is chosen from the group consisting of the fifteen amino alcohol residues of Table 2-1;

$R^2$ is chosen from the group consisting of the thirty-one carboxylic acid residues of Table 2-2;

$R^3$ and $R^4$ are independently selected from the group consisting of the twelve amine residues of Table 2-4; and $R^9$ is chosen from the five residues of Table 2-5.

Yet another preferred embodiment of the invention is a library comprising a plurality of members of Formula IV wherein:

$R^1$ is 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl or 4-phenylbenzyl.

A further preferred embodiment of the invention is a library comprising a plurality of members of Formula IV wherein:

$R^2$ is (N-benzyloxycarbonyl)pyrrolidin-2-yl, 4-butoxyphenyl, 4-chlorophenoxymethyl, cyclohexyl, 2-cyclopentylethyl, cyclopropyl, 3,4-dichlorophenyl, 2,3-difluorophenyl, 2,4-dimethoxyphenyl, 3-(3,4-dimethoxyphenyl)propyl, 2,6-dimethylphenoxymethyl, 2,2-dimethylpropyl, 2,2-diphenylethyl, 2-fluoro-4-trifluoromethylphenyl, 2-furanyl, indan-2-ylmethyl, 4-(2-methoxy)ethoxyphenethyl, 3-methylbutyl, 1-naphthyl, 2-naphthyloxymethyl, pentyl, 4-phenoxyphenyl, phenyl, 4-(phenyl)phenyl, 3-phenylpropyl, 3-pyridinyl, 3-quinolinyl or one of the following residues:

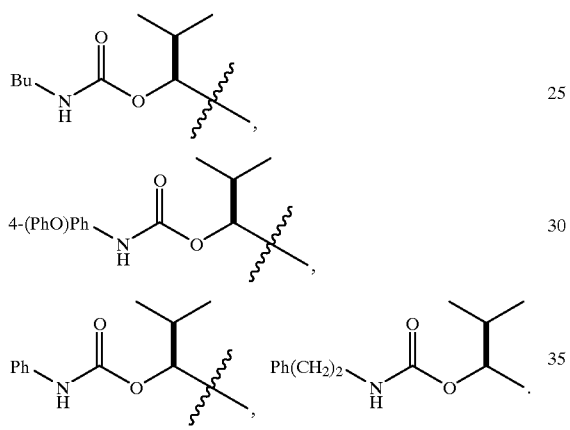

A preferred embodiment of the invention is a library comprising a plurality of members of Formula IV wherein:

$R^3$ and $R^4$ are independently selected from the group consisting of hydrogen, 2-benzamidazolylmethyl, N-benzylpiperidin-4-yl, N-benzylpyrrolidin-3-yl, butyl, 3-imidazolylprop-1-yl, 3-phenylhydroxyprop-2-yl, 1,2-diphenylhydroxyeth-2-yl,

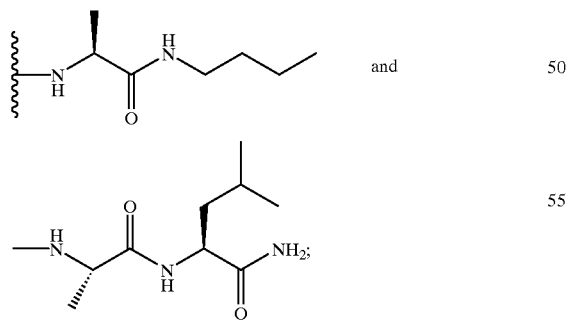

or $R^3$ and $R^4$ together are 3-carboxamidopiperidinyl or 4-methylpiperazinyl.

Yet another preferred embodiment of the invention is a library comprising a plurality of members of Formula IV wherein:

$R^9$ is allyl, butyl, ethyl, propyl or benzyl.

Another embodiment of the invention is a method of synthesizing a library comprising a plurality of members of the formula:

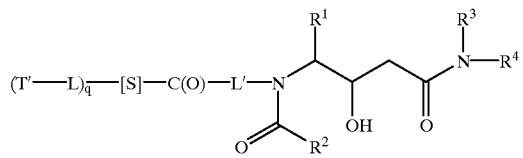

which comprises:

a. attaching a protected amino alcohol of the formula:

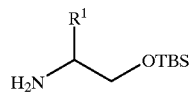

to a solid support suspended in tetrahydrofuran to form a resin-linked protected β-hydroxy amine of the formula:

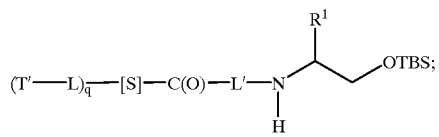

b. coupling the resin-linked protected β-hydroxy amine in pyridine with an acid chloride to provide a resin-linked protected β-hydroxy amide of the formula:

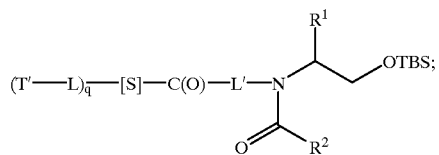

c. treating the resin-linked protected β-hydroxy amide in an alcohol solvent with dilute acid to form an intermediate resin-linked β-hydroxy amide of the formula:

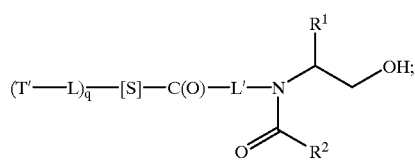

d. treating the intermediate resin-linked β-hydroxy amide with a mild oxidizing agent to form a resin-linked aldehyde of the formula:

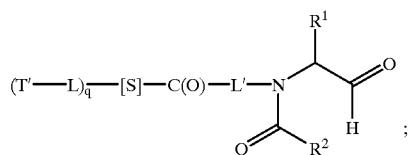

e. treating the resin-linked aldehyde in tetrahydrofuran with allyl(triphenylphosphoranylidene)acetate to provide a resin-linked α,β-unsaturated allyl ester of the formula:

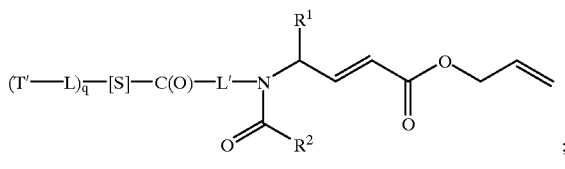

f. treating the resin-linked α,β-unsaturated allyl ester in anhydrous solvent with tetrakis(triphenylphosphine) palladium(0) and morpholine to form a resin-linked α,β-unsaturated carboxylic acid of the formula:

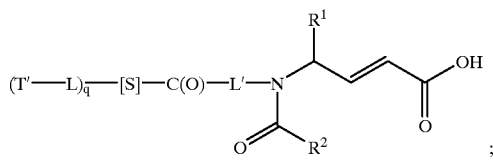

g. treating the resin-linked α,β-unsaturated carboxylic acid in dimethylformamide and pyridine with a mixture of pentafluorophenyl trifluoroacetate and pentafluorophenol to provide a resin-linked intermediate α,β-unsaturated pentafluorophenyl ester of the formula:

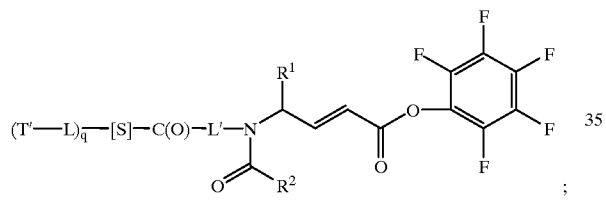

h. treating the resin-linked α,β-unsaturated pentafluorophenyl ester in dimethylformamide with an amine to form a resin-linked α,β-unsaturated diamide of the formula:

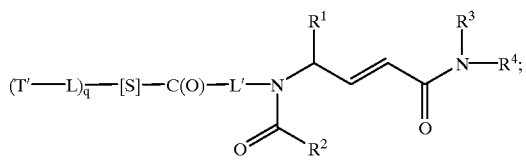

and i. treating the resin-linked α,β-unsaturated diamide with trifluoroacetic acid, followed by treatment in dichloromethane with triethylamine to provide a resin-linked hydroxy amide of the formula:

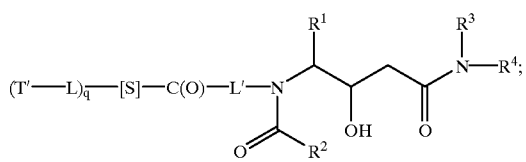

wherein:
T' is a tag;
L is a first linker;
T'-L- together form an identifier residue;
q is 0–30;
[S] is a solid support;
$R^1$ is chosen from the group consisting of alkyl, aralkyl, aryl, $-(CH_2)_n-NHC(O)R^5$ and $-(CH_2)_n$-cycloalkyl; where n=1–4;
$R^2$ is chosen from the group consisting of alkyl, aralkyl, aryl, aryloxyalkyl, cycloalkyl, $-(CH_2)_n$-cycloalkyl, heteroaryl, $-CH(R^6)OC(O)NHR^5$,

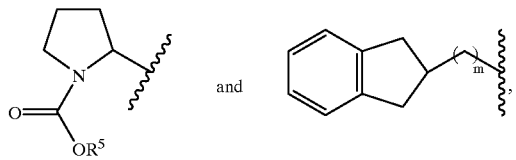

wherein m=0–3; or $R^2$ is the descarboxy residue of an N-capped-α-amino acid;
$R^3$ and $R^4$ are independently selected from the group consisting of H, alkyl, aralkyl, heteroarylalkyl, heterocycloalkyl, $-CH(R^5)CH(R^6)OH$, $-CH(R^5)C(O)NHR^6$ and $-CH(R^5)C(O)NHCH(R^6)C(O)NHR^7$; or
$R^3$ and $R^4$ together are

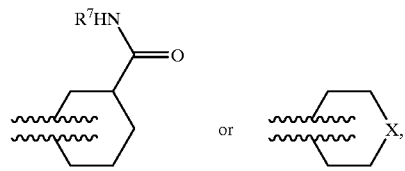

wherein X=O or $NR^8$;
$R^5$ are independently selected from the group consisting of alkyl, aralkyl and aryl;
$R^6$ is H, lower alkyl, aryl or aralkyl;
$R^7$ is H or alkyl; and
$R^8$ is chosen from the group consisting of H, $R^5$, $C(O)R^5$, $C(O)OR^5$ and $-SO_2R^5$.

Preferably, $R^1$ is chosen from the group consisting of the fifteen amino alcohol residues of Table 2-1. $R^2$ is chosen from the group consisting of the thirty-one carboxylic acid residues of Table 2-2. $R^3$ and $R^4$ are independently selected from the group consisting of the twelve amine residues of Table 2-4.

Preferably, $R^1$ is 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl or 4-phenylbenzyl. $R^2$ is (N-benzyloxycarbonyl)pyrrolidin-2-yl, 4-butoxyphenyl, 4-chlorophenoxymethyl, cyclohexyl, 2-cyclopentylethyl, cyclopropyl, 3,4-dichlorophenyl, 2,3-difluorophenyl, 2,4-dimethoxyphenyl, 3-(3,4-dimethoxyphenyl)propyl, 2,6-dimethylphenoxymethyl, 2,2-dimethylpropyl, 2,2-diphenylethyl, 2-fluoro-4-trifluoromethylphenyl, 2-furanyl, indan-2-ylmethyl, 4-(2-methoxy)ethoxyphenethyl, 3-methylbutyl, 1-naphthyl, 2-naphthyloxymethyl, pentyl, 4-phenoxyphenyl, phenyl, 4-(phenyl)phenyl, 3-phenylpropyl, 3-pyridinyl, 3-quinolinyl or one of the following residues:

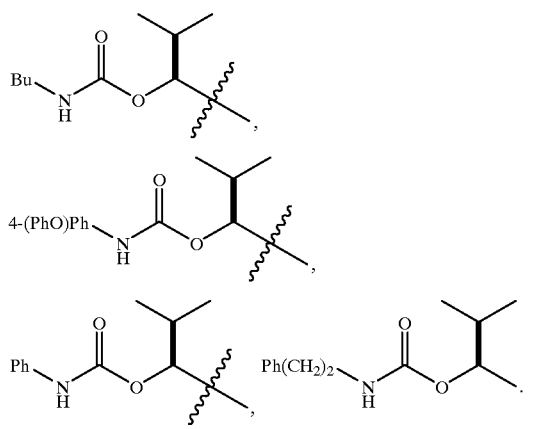

$R^3$ and $R^4$ are independently selected from hydrogen, 2-benzamidazolylmethyl, N-benzylpiperidin-4-yl, N-benzylpyrrolidin-3-yl, butyl, 3-imidazolylprop-1-yl, 3-phenylhydroxyprop-2-yl, 1,2-diphenylhydroxyeth-2-yl,

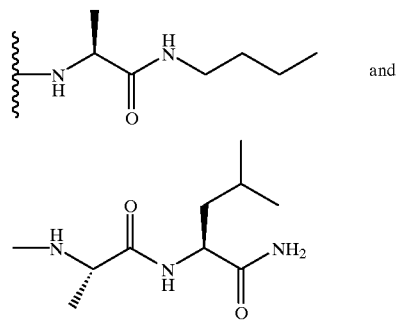

and

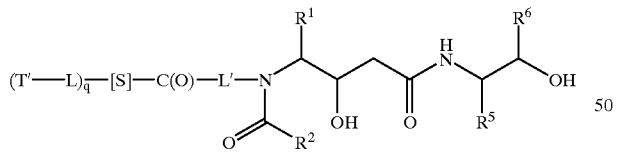

or $R^3$ and $R^4$ together are 3-carboxamidopiperidinyl or 4-methylpiperazinyl.

A preferred embodiment of the invention is a method of synthesizing a library comprising a plurality of members of the formula:

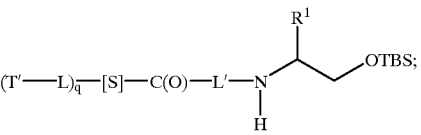

which comprises:

a. attaching a protected amino alcohol of the formula:

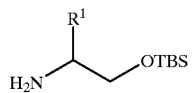

to a solid support suspended in tetrahydrofuran to form a resin-linked protected β-hydroxy amine of the formula:

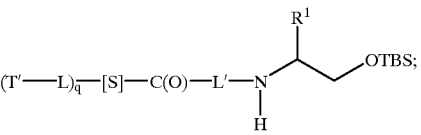

b. coupling the resin-linked protected β-hydroxy amine in pyridine with an acid chloride to provide a resin-linked protected β-hydroxy amide of the formula:

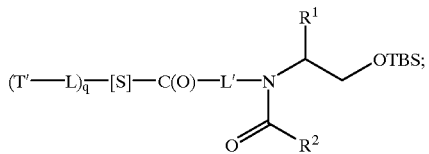

c. treating the resin-linked protected β-hydroxy amide in an alcohol solvent with dilute acid to form an intermediate resin-linked β-hydroxy amide of the formula:

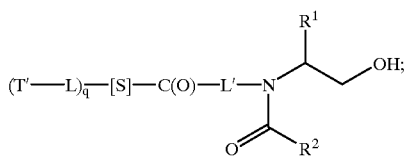

d. treating the intermediate resin-linked β-hydroxy amide with a mild oxidizing agent to form a resin-linked aldehyde of the formula:

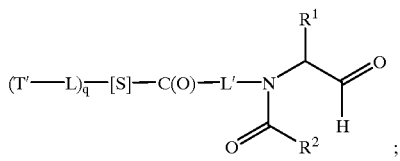

e. treating the resin-linked aldehyde in tetrahydrofuran with allyl(triphenylphosphoranylidene)acetate to provide a resin-linked α,β-unsaturated allyl ester of the formula:

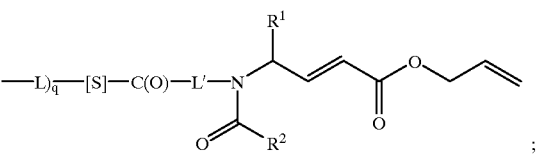

f. treating the resin-linked α,β-unsaturated allyl ester in an anhydrous solvent with tetrakis(triphenylphosphine) palladium(0) and morpholine to form a resin-linked α,β-unsaturated carboxylic acid of the formula:

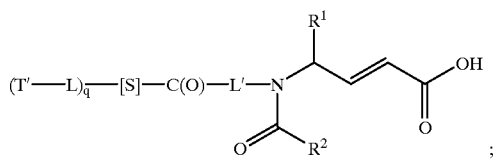

g. treating the resin-linked α,β-unsaturated carboxylic acid in dimethylformamide and pyridine with a mixture of pentafluorophenyl trifluoroacetate and pentafluorophenol to provide a resin-linked intermediate α,β-unsaturated pentafluorophenyl ester of the formula:

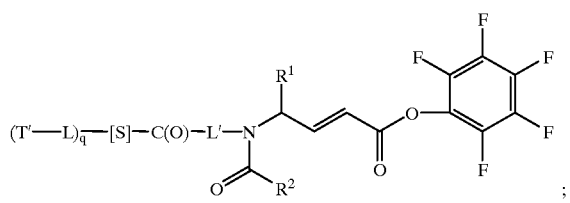

h. treating the resin-linked pentafluorophenyl ester in dimethylformamide with a β-hydroxy amine to produce a resin-linked amide of the formula:

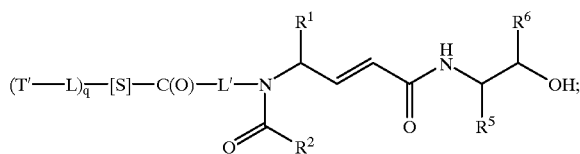

i. treating the resin-linked amide in pyridine with acetic anhydride in the presence of dimethylaminopyridine to produce a resin-linked acetoxy amide of the formula:

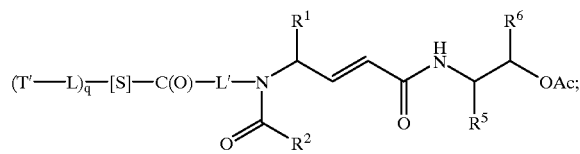

j. treating the resin-linked acetoxy amide with trifluoroacetic acid, followed by treatment in dichloromethane with triethylamine to produce a resin-linked acetoxy hydroxy amide of the formula:

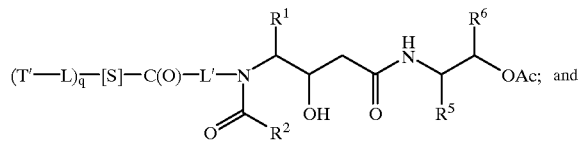

k. treating the resin-linked acetoxy hydroxy amide in an alcohol solvent with hydrazine to produce a resin-linked dihydroxy amide of the formula:

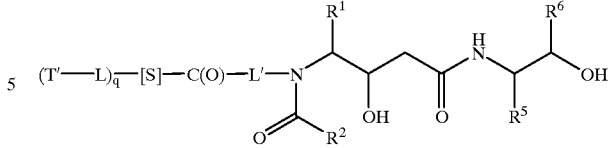

wherein:

T' is a tag;

L is a first linker;

T'-L- together form an identifier residue;

q is 0–30;

[S] is a solid support;

$R^1$ is chosen from the group consisting of alkyl, aralkyl, aryl, —$(CH_2)_n$—$NHC(O)R^5$ and —$(CH_2)_n$-cycloalkyl; where n=1–4;

$R^2$ is chosen from the group consisting of alkyl, aralkyl, aryl, aryloxyalkyl, cycloalkyl, —$(CH_2)_n$-cycloalkyl, heteroaryl, —$CH(R^6)OC(O)NHR^5$,

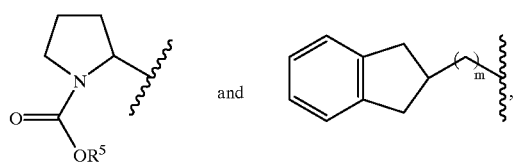

wherein m=0–3; or $R^2$ is the descarboxy residue of an N-capped-α-amino acid;

$R^5$ are independently selected from the group consisting of alkyl, aralkyl and aryl; and $R^6$ is H, lower alkyl, aryl or aralkyl.

Preferably, $R^1$ is chosen from the group consisting of the fifteen amine residues of Table 2-1. $R^2$ is chosen from the group consisting of the thirty-one acid residues of Table 2-2. $R^5$ is benzyl, butyl, methyl, phenethyl, phenoxyphenyl or phenyl and $R^6$ is benzyl, butyl, hydrogen, isobutyl or phenyl.

Preferably, $R^1$ is 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl or 4-phenylbenzyl. $R^2$ is (N-benzyloxycarbonyl)pyrrolidin-2-yl, 4-butoxyphenyl, 4-chlorophenoxymethyl, cyclohexyl, 2-cyclopentylethyl, cyclopropyl, 3,4-dichlorophenyl, 2,3-difluorophenyl, 2,4-dimethoxyphenyl, 3-(3,4-dimethoxyphenyl)propyl, 2,6-dimethylphenoxymethyl, 2,2-dimethylpropyl, 2,2-diphenylethyl, 2-fluoro-4-trifluoromethylphenyl, 2-furanyl, indan-2-ylmethyl, 4-(2-methoxy)ethoxyphenethyl, 3-methylbutyl, 1-naphthyl, 2-naphthyloxymethyl, pentyl, 4-phenoxyphenyl, phenyl, 4-(phenyl)phenyl, 3-phenylpropyl, 3-pyridinyl, 3-quinolinyl or one of the following residues:

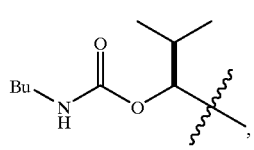

-continued

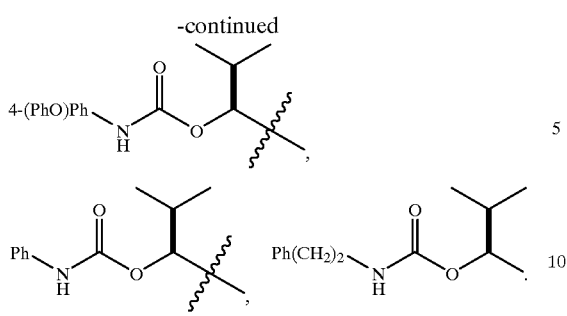

A preferred embodiment of the invention is a method of synthesizing a library comprising a plurality of members of the formula:

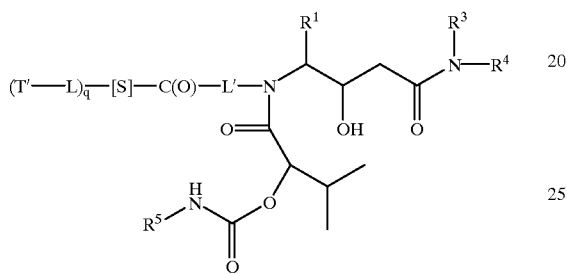

which comprises:

a. attaching a protected amino alcohol of the formula:

to a solid support suspended in tetrahydrofuran to form a resin-linked protected β-hydroxy amine of the formula:

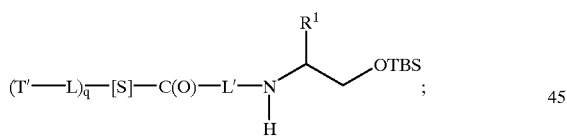

b. coupling 2-chloroacetoxy isovaleryl chloride in pyridine with the resin-linked protected β-hydroxy amine to produce a resin-linked protected β-hydroxy amide of the formula:

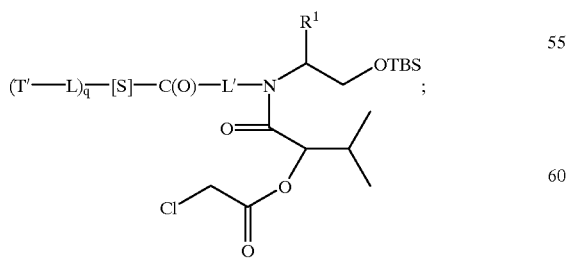

c. treating the resin-linked protected β-hydroxy amide in an alcohol solvent with hydrazine to form a resin-linked protected β-hydroxy amido-alcohol of the formula:

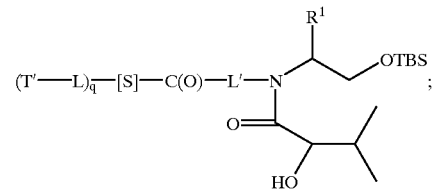

d. treating the resin-linked protected β-hydroxy amido-alcohol in an anhydrous solvent with an isocyanate in the presence of a base to produce a resin-linked protected β-hydroxy amido-carbamate of the formula:

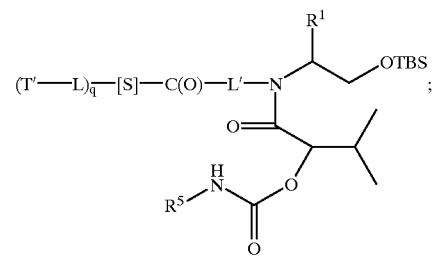

e. treating the resin-linked protected β-hydroxy amido-carbamate in methanol with dilute acid to form an intermediate resin-linked β-hydroxy amido-carbamate of the formula:

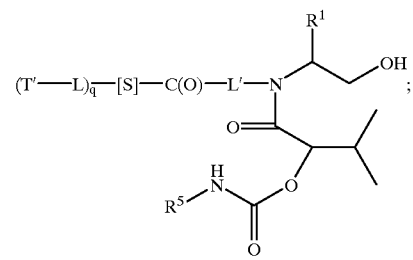

f. treating the intermediate resin-linked β-hydroxy amido-carbamate with a mild oxidizing agent produce a resin-linked aldehyde of the formula:

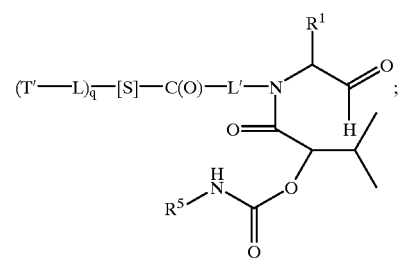

g. coupling the resin-linked aldehyde with allyl (triphenylphosphoranylidene)acetate to produce a resin-linked α,β-unsaturated allyl ester of the formula:

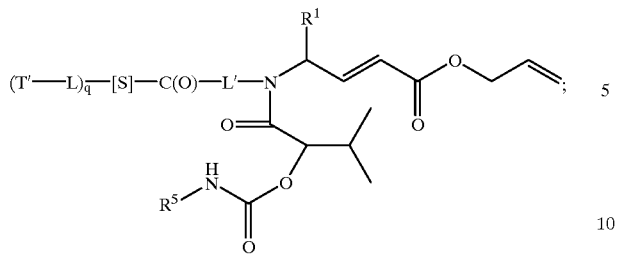

h. cleaving the resin-linked α,β-unsaturated allyl ester in an anhydrous solvent with tetrakis(triphenylphosphine) palladium(0) in the presence of morpholine to produce a resin-linked α,β-unsaturated carboxylic acid of the formula:

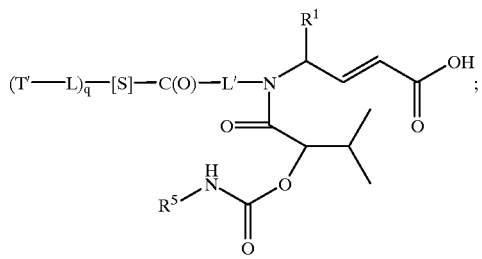

i.. treating the resin-linked α,β-unsaturated carboxylic acid in dimethylformamide and pyridine with a mixture of pentafluorophenyl trifluoroacetate and pentafluorophenol to produce an intermediate resin-linked pentafluorophenyl ester of the formula:

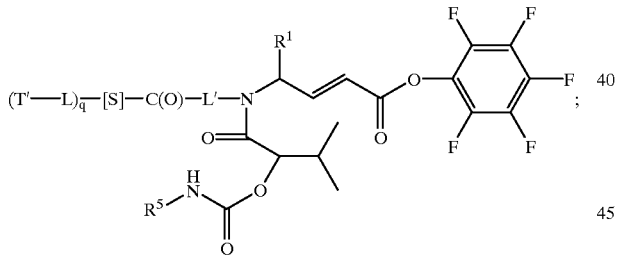

j. treating the intermediate resin-linked pentafluorophenyl ester in dimethylformamide with an amine to form a resin-linked diamide of the formula:

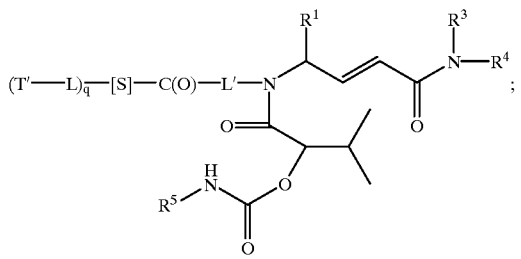

and k. treating the resin-linked diamide with trifluoroacetic acid, followed by treatment in dichloromethane with triethylamine to produce a resin-linked hydroxy amide of the formula:

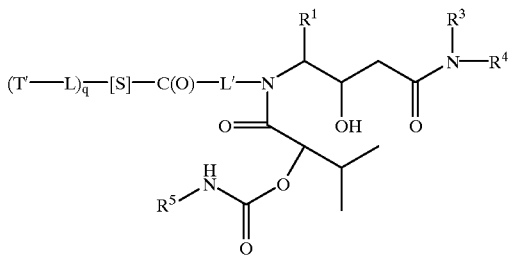

wherein:

T' is a tag;

L is a first linker;

T'-L- together form an identifier residue;

q is 0–30;

[S] is a solid support;

$R^1$ is chosen from the group consisting of alkyl, aralkyl, aryl, —$(CH_2)_n$—$NHC(O)R^5$ and —$(CH_2)_n$-cycloalkyl; where n=1–4;

$R^3$ and $R^4$ are independently selected from the group consisting of H, alkyl, aralkyl, heteroarylalkyl, heterocycloalkyl, —$CH(R^5)CH(R^6)OH$, —$CH(R^5)C(O)NHR^6$ and —$CH(R^5)C(O)NHCH(R^6)C(O)NHR^7$; or $R^3$ and $R^4$ together are

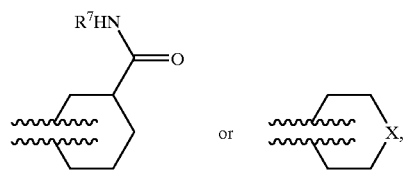

wherein X=O or $NR^8$;

$R^5$ are independently selected from the group consisting of alkyl, aralkyl or aryl;

$R^6$ is H, lower alkyl, aryl or aralkyl;

$R^7$ is H or alkyl; and $R^8$ is chosen from the group consisting of H, $R^5$, $C(O)R^5$, $C(O)OR^5$ and —$SO_2R^5$.

Preferably, $R^1$ is chosen from the group consisting of the fifteen amine residues of Table 2-1. $R^3$ and $R^4$ are independently selected from the group consisting of the twelve amine residues of Table 2-4. $R^5$ is butyl, phenethyl, phenoxyphenyl or phenyl.

Preferably, $R^1$ is 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl or 4-phenylbenzyl. $R^3$ and $R^4$ are independently selected from the group consisting of hydrogen, 2-benzamidazolylmethyl, N-benzylpiperidin-4-yl, N-benzylpyrrolidin-3-yl, butyl, 3-imidazolylprop-1-yl, 3-phenylhydroxyprop-2-yl, 1,2-diphenylhydroxyeth-2-yl,

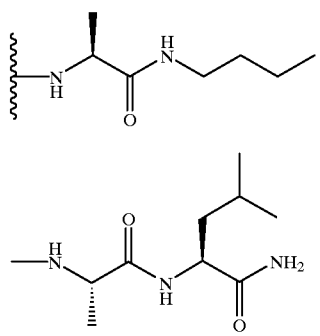

or $R^3$ and $R^4$ together are 3-carboxamidopiperidinyl or 4-methylpiperazinyl.

A preferred embodiment of the invention is a method of synthesizing a library comprising a plurality of members of the formula:

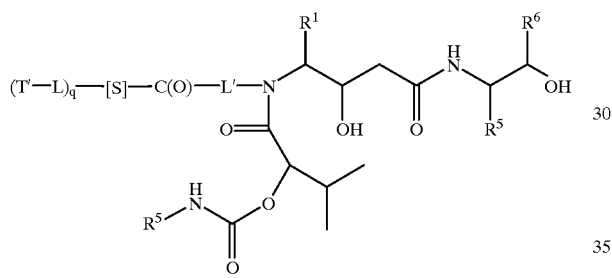

which comprises:

a. attaching a protected amino alcohol of the formula:

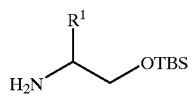

to a solid support suspended in tetrahydrofuran to form a resin-linked protected β-hydroxy amine of the formula:

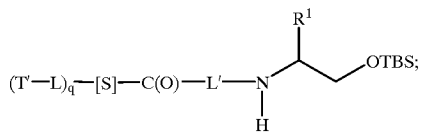

b. coupling 2-chloroacetoxy isovaleryl chloride in pyridine with the resin-linked protected β-hydroxy amine to produce a resin-linked protected β-hydroxy amide of the formula:

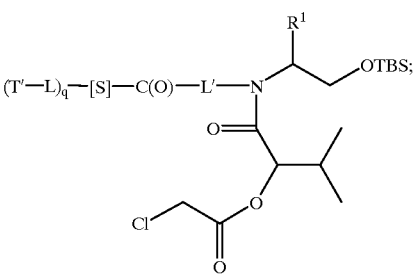

c. treating the resin-linked protected β-hydroxy amide in an alcohol solvent with hydrazine to form a resin-linked protected β-hydroxy amido-alcohol of the formula:

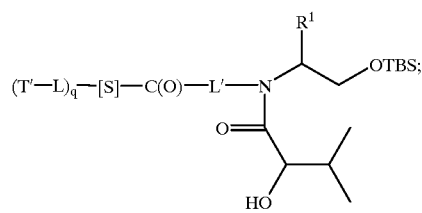

d. treating the resin-linked protected β-hydroxy amido-alcohol in an anhydrous solvent with an isocyanate in the presence of a base to produce a resin-linked protected β-hydroxy amido-carbamate of the formula:

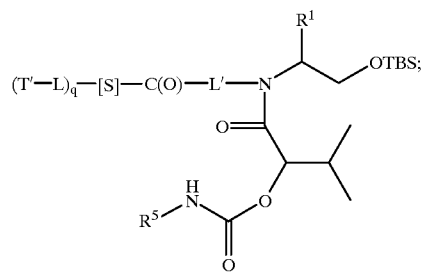

e. treating the resin-linked protected β-hydroxy amido-carbamate in methanol with dilute acid to form an intermediate resin-linked β-hydroxy amido-carbamate of the formula:

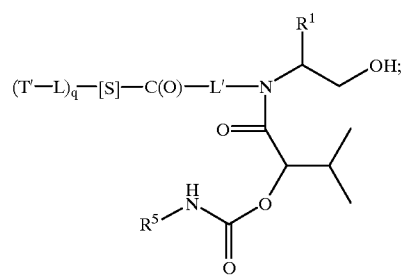

f. treating the intermediate resin-linked β-hydroxy amido-carbamate with a mild oxidizing agent to produce a resin-linked amido-carbamate aldehyde of the formula:

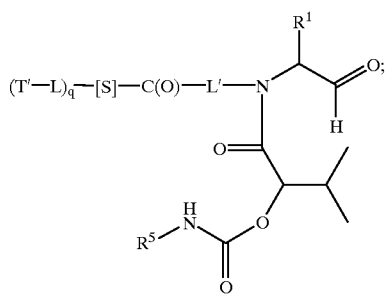

g. coupling the resin-linked amido-carbamate aldehyde with allyl(triphenylphosphoranylidene)acetate to produce a resin-linked α,β-unsaturated allyl ester of the formula:

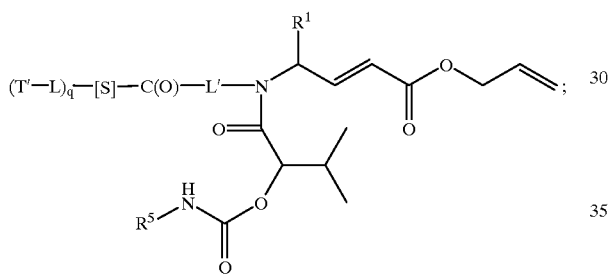

h. cleaving the resin-linked α,β-unsaturated allyl ester in an anhydrous solvent with tetrakis(triphenylphosphine)palladium(0) in the presence of morpholine to produce a resin-linked α,β-unsaturated carboxylic acid of the formula:

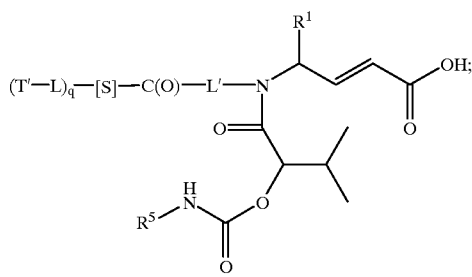

i. treating the resin-linked α,β-unsaturated carboxylic acid in dimethylformamide and pyridine with a mixture of pentafluorophenyl trifluoroacetate and pentafluorophenol to produce an intermediate resin-linked pentafluorophenyl ester of the formula:

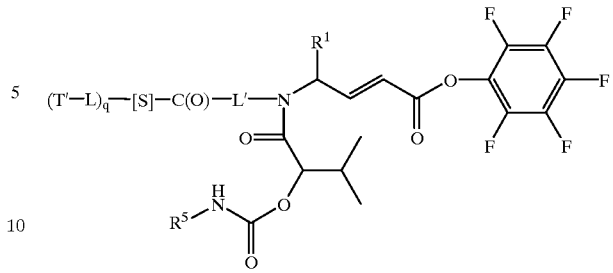

j. treating the resin-linked pentafluorophenyl ester in dimethylformamide with a β-hydroxy amine to produce a resin-linked amide of the formula:

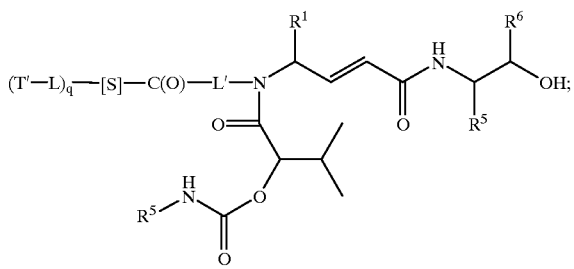

k. treating the resin-linked amide in pyridine with acetic anhydride in the presence of dimethylaminopyridine to produce a resin-linked acetoxy amide of the formula:

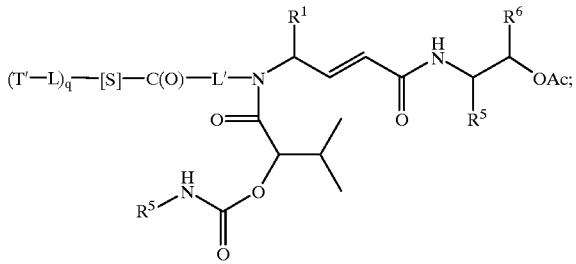

l. treating the resin-linked acetoxy amide with trifluoroacetic acid, followed by treatment in dichloromethane with triethylamine to produce a resin-linked acetoxy hydroxy amide of the formula:

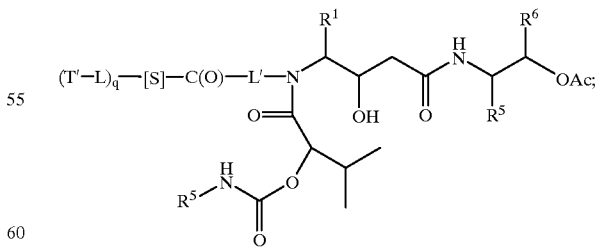

and m. treating the resin-linked acetoxy hydroxy amide in an alcohol solvent with hydrazine to produce a resin-linked dihydroxy amide of the formula:

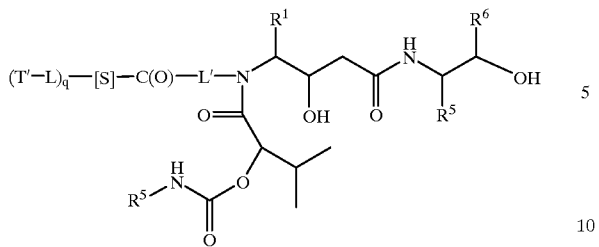

wherein:
T' is a tag;
L is a first linker;
T'-L- together form an identifier residue;
q is 0–30;
[S] is a solid support;
R¹ is chosen from the group consisting of alkyl, aralkyl, aryl, —(CH$_2$)$_n$—NHC(O)R⁵ and —(CH$_2$)$_n$-cycloalkyl; where n=1–4;
R⁵ are independently selected from the group consisting of alkyl, aralkyl and aryl; and
R⁶ is H, lower alkyl, aryl or aralkyl.

Preferably, R¹ is chosen from the group consisting of the fifteen amine residues of Table 2-1. R⁵ are independently selected from the group consisting of benzyl, butyl, methyl, phenethyl, phenoxyphenyl and phenyl and R⁶ is benzyl, butyl, hydrogen, isobutyl or phenyl.

Preferably, R¹ is 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl or 4-phenylbenzyl.

Another embodiment of the invention is a method of synthesizing a library comprising a plurality of members of the formula:

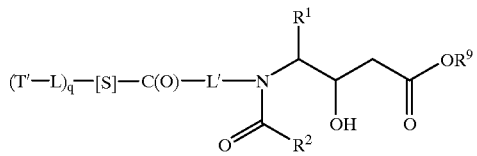

which comprises:
a. attaching a protected amino alcohol of the formula:

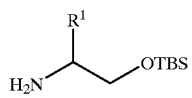

to a solid support suspended in tetrahydrofuran to form a resin-linked protected β-hydroxy amine of the formula:

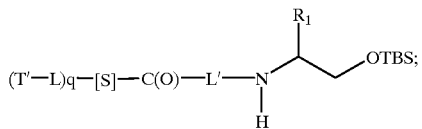

b. coupling the resin-linked protected β-hydroxy amine in pyridine with an acid chloride to provide a resin-linked protected β-hydroxy amide of the formula:

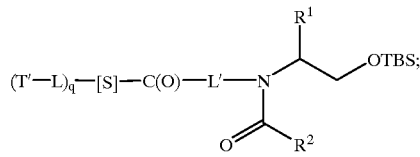

c. treating the resin-linked protected β-hydroxy amide in an alcohol solvent with dilute acid to form an intermediate resin-linked β-hydroxy amide of the formula:

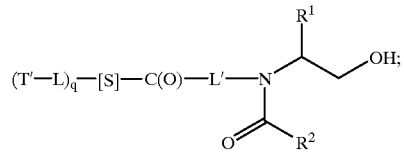

d. treating the intermediate resin-linked β-hydroxy amide with a mild oxidizing agent to form a resin-linked aldehyde of the formula:

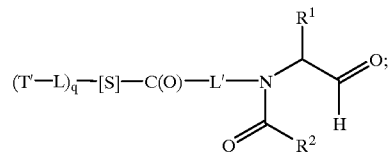

e. treating the resin-linked amide aldehyde in tetrahydrofuran with a (triphenylphosphoranylidene)acetate ester to provide a resin-linked α,β-unsaturated ester of the formula:

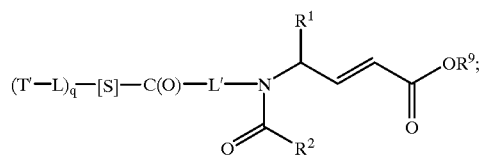

and
f. treating the resin-linked α,β-unsaturated ester with trifluoroacetic acid, followed by treatment with triethylamine in dichloromethane to provide a resin-linked hydroxy amide of the formula:

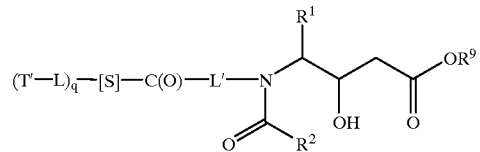

wherein:
T' is a tag;
L is a first linker;
T'-L- together form an identifier residue;
q is 0–30;
[S] is a solid support;
R¹ is chosen from the group consisting of alkyl, aralkyl, aryl, —(CH$_2$)$_n$—NHC(O)R⁵ and —(CH$_2$)$_n$-cycloalkyl; where n=1–4;

R² is chosen from the group consisting of alkyl, aralkyl, aryl, aryloxyalkyl, cycloalkyl, —(CH₂)ₙ-cycloalkyl, heteroaryl, —CH(R⁶)OC(O)NHR⁵,

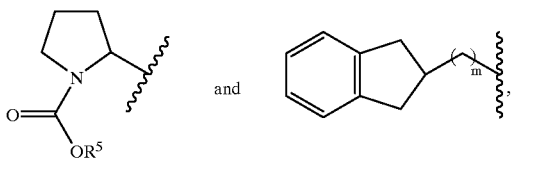

wherein m=0–3; or R² is the descarboxy residue of an N-capped-α-amino acid; and

R⁵ are independently selected from the group consisting of alkyl, aralkyl and aryl;

R⁶ is H, lower alkyl, aryl or aralkyl;

R⁷ is H or alkyl; and

R⁹ is alkyl, aryl, aralkyl or R⁷CH=CH(CH₂)ₙ.

Preferably, R¹ is chosen from the group consisting of the fifteen amine residues of Table 2-1. R² is chosen from the group consisting of the thirty-one acid residues of Table 2-2. R⁹ is chosen from the group consisting of the five (triphenylphosphoranylidene)acetate ester residues in Table 2-5.

Preferably, R¹ is 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl or 4-phenylbenzyl. R² is (N-benzyloxycarbonyl)pyrrolidin-2-yl, 4-butoxyphenyl, 4-chlorophenoxymethyl, cyclohexyl, 2-cyclopentylethyl, cyclopropyl, 3,4-dichlorophenyl, 2,3-difluorophenyl, 2,4-dimethoxyphenyl, 3-(3,4-dimethoxyphenyl)propyl, 2,6-dimethylphenoxymethyl, 2,2-dimethylpropyl, 2,2-diphenylethyl, 2-fluoro-4-trifluoromethylphenyl, 2-furanyl, indan-2-ylmethyl, 4-(2-methoxy)ethoxyphenethyl, 3-methylbutyl, 1-naphthyl, 2-naphthyloxymethyl, pentyl, 4-phenoxyphenyl, phenyl, 4-(phenyl)phenyl, 3-phenylpropyl, 3-pyridinyl, 3-quinolinyl or one of the following residues:

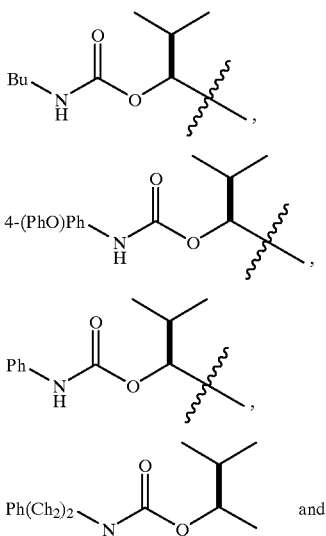

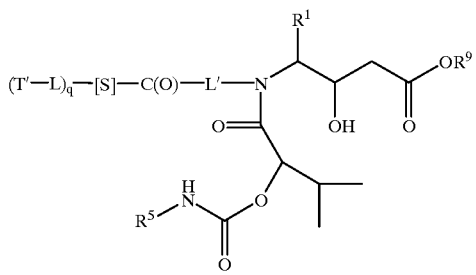

R⁹ is ethyl, allyl, propyl, butyl or benzyl.

A preferred embodiment of the invention is a method of synthesizing a library comprising a plurality of members of the formula:

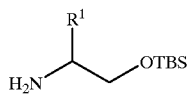

which comprises:

a. attaching a protected amino alcohol of the formula:

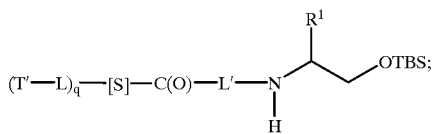

to a solid support suspended in tetrahydrofuran to form a resin-linked protected β-hydroxy amine of the formula:

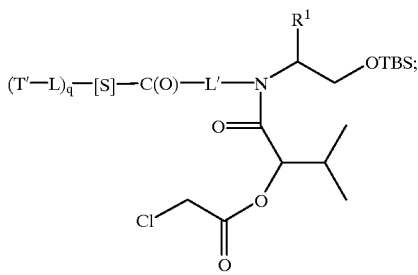

b. coupling 2-chloroacetoxy isovaleryl chloride in pyridine with the resin-linked protected β-hydroxy amine to produce a resin-linked protected β-hydroxy amide of the formula:

c. treating the resin-linked protected β-hydroxy amide in an alcohol solvent with hydrazine to form a resin-linked protected β-hydroxy amido-alcohol of the formula:

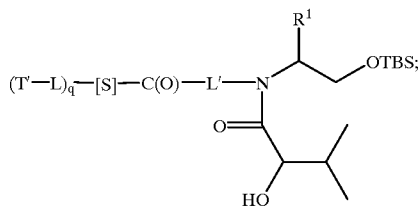

d. treating the resin-linked protected β-hydroxy amido-alcohol in an anhydrous solvent with an isocyanate in the presence of a base to produce a resin-linked protected β-hydroxy amido-carbamate of the formula:

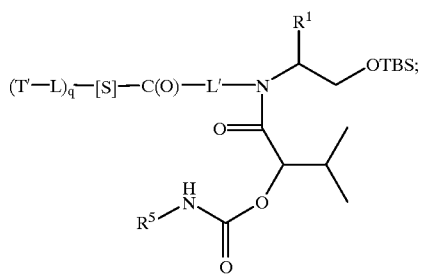

e. treating the resin-linked protected β-hydroxy amido-carbamate in methanol with dilute acid to form an intermediate resin-linked β-hydroxy amido-carbamate of the formula:

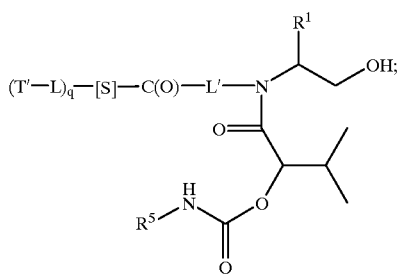

f. treating the intermediate resin-linked β-hydroxy amido-carbamate with a mild oxidizing agent produce a resin-linked aldehyde of the formula:

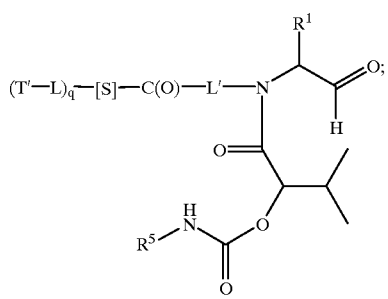

g. coupling the resin-linked amide aldehyde with a (triphenylphosphoranylidene)acetate ester to produce a resin-linked α,β-unsaturated ester of the formula:

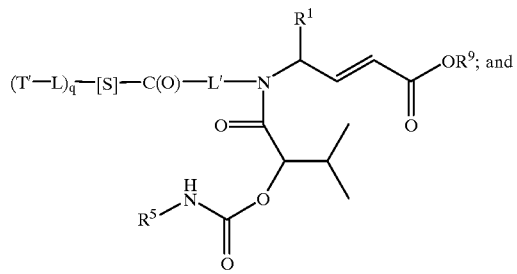

h. treating the resin-linked ester with trifluoroacetic acid, followed by treatment with triethylamine in dichloromethane to produce a resin-linked hydroxy amide of the formula:

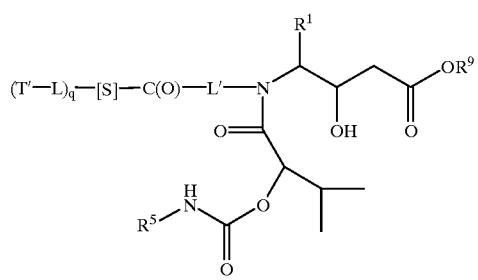

wherein:

T' is a tag;

L is a first linker;

T'-L- together form an identifier residue;

q is 0–30;

[S] is a solid support;

$R^1$ is chosen from the group consisting of alkyl, aralkyl, aryl, —$(CH_2)_n$—$NHC(O)R^5$ and —$(CH_2)_n$-cycloalkyl; where n=1–4;

$R^5$ are independently selected from the group consisting of alkyl, aralkyl and aryl; and $R^7$ is H or alkyl; and $R^9$ is alkyl, aryl, aralkyl or $R^7CH=CH(CH_2)_n$.

Preferably, $R^1$ is chosen from the group consisting of the fifteen amino alcohol residues of Table 2-1. $R^5$ is butyl, phenethyl, phenoxyphenyl or phenyl and $R^9$ is chosen from the group consisting of the five (triphenylphosphoranylidene)acetate ester residues in Table 2-5.

Preferably, $R^1$ is 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl or 4-phenylbenzyl. $R^9$ is ethyl, allyl, propyl, butyl or benzyl.

A preferred embodiment of the invention is a method of synthesizing a library comprising a plurality of members of Formula I which comprises cleaving the resin-linked hydroxy amide from the resin to provide a hydroxy amide of the formula:

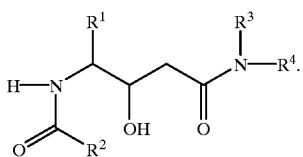

A preferred embodiment of the invention is a method of synthesizing a library comprising a plurality of members of Formula I which comprises cleaving the resin-linked dihydroxy amide from the resin to provide a dihydroxy amide of the formula:

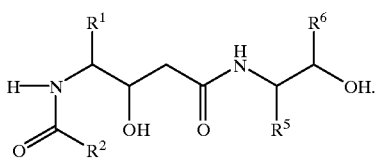

A preferred embodiment of the invention is a method of synthesizing a library comprising a plurality of members of Formula I which comprises cleaving the resin-linked hydroxy amide from the resin to provide a hydroxy amide of the formula:

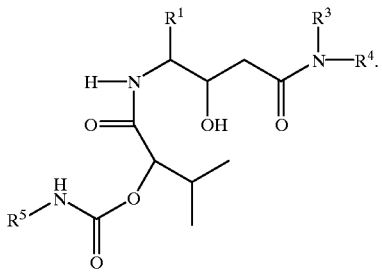

A preferred embodiment of the invention is a method of synthesizing a library comprising a plurality of members of Formula I which comprises cleaving the resin-linked dihydroxy amide from the resin to provide a dihydroxy amide of the formula:

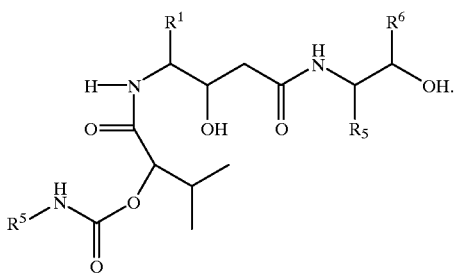

A preferred embodiment of the invention is a method of synthesizing a library comprising a plurality of members of Formula I which comprises cleaving the resin-linked hydroxy amide from the resin to provide a hydroxy amide of the formula:

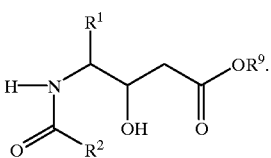

A preferred embodiment of the invention is a method of synthesizing a library comprising a plurality of members of Formula I which comprises cleaving the resin-linked hydroxy amide from the resin to provide a hydroxy amide of the formula:

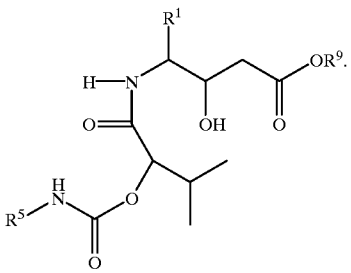

II. Utility

Another aspect of the invention is the use of the combinatorial library of Formula I in assays to discovery biologically active compounds or ligands of Formula III. Thus another aspect of the invention is a method for identifying a compound having a desired characteristic, which comprises synthesizing a combinatorial library of Formula I and testing the library, either attached to (i.e. Formula I) or detached from (i.e. Formula III) the solid supports, in an assay which identifies compounds having the desired characteristic.

A further aspect of the invention is determining the structure of any compound so identified. It is within the scope of the present invention that chemical structures of compounds identified as having a desired characteristic can be determined by either decoding the tags (T, T'-L- of Formula I) or by deconvolution of the library (Smith et al., BioMed. Chem. Lett. 4, 2821 (1994); Kurth et al., J. Org. Chem. 59, 5862 (1994); Murphy et al., J. Am. Chem. Soc. 117, 7029 (1995); Campell et al., J. Am. Chem. Soc. 118, 5381 (1995); and Erb et al., Proc. Natl. Acad. Sci. USA 91, 11422 (1994)). In addition, decoding or deconvolution procedures may be verified by analysis of the cleaved compound, such as by mass spectrometry.

The "linkers" may be any component capable of being selectively cleaved to release both T and Z from the solid support (See, Greene and Wuts, "Protective Groups in Organic Synthesis," 2nd ed., Wiley, 1991). Specific linkers L' are depicted in Table 1 which also shows cleavage reagents. In designing a synthetic scheme, L and L' are chosen such that they are orthogonally reactive, i.e., they allow for removal of either T or Z (where T=T'OH) without removal of the other, since simultaneous cleavage of both T and Z from the solid support is disadvantageous. In the structures as shown, the left-hand bond is the point of attachment to the solid support (via —C(O)— for L' and —C(O)— or —CH$_2$C(O)— for L) and the right-hand bond is the point of attachment to either T or Z.

The tags of this invention, T, are chemical entities which possess several properties: they are detachable from the solid supports, preferably by photolysis or oxidation; they are individually differentiable, and preferably separable;

they are stable under the synthetic conditions; and they are capable of being detected at very low concentrations, e.g., $10^{-18}$ to $10^{-9}$ mole. Preferred tags are identifiable with readily available equipment which does not require sophisticated technical capabilities to operate, and they are relatively economical. The tags may be structurally related or unrelated, e.g., a homologous series, repetitive functional groups, related members of the Periodic Chart, different isotopes, combinations thereof, and the like. At the end of the combinatorial synthesis there will usually be attached at least 0.01 femtomol, usually 0.001–50 pmol, of each tag to each solid support. The tags may be comprised of alkyl, alkenyl, alkoxy, cycloalkyl, aryl, aryloxy, heterocycloalkyl or heteroaryl groups, or combinations thereof. Distinguishing features may be the number of repetitive units, such as methylene groups in an alkyl moiety; alkenyloxy groups in a polyalkenyloxy moiety; halo groups in a polyhalo compound; α- and/or β-substituted ethylene groups where the substituents may be alkyl groups, alkoxy, carboxyalkyl, amino, halo, or the like; isotopes; etc. Suitable tags and methods for their employment are described in U.S. Pat. No. 5,565,324, the entire disclosure of which is incorporated herein by reference.

The materials upon which the combinatorial syntheses of the present invention are performed are referred to as solid supports, beads, and resins. These terms are intended to include:

(a) beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b) soluble supports such as low molecular weight non-cross-linked polystyrene. TentaGel™ $NH_2$ (available from Rapp Polymere, Tubingen, Germany) is an amine functionalized polyethylene glycol-grafted polystyrene resin.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R) or (S), or as (D) or (L) for amino acids. The present invention is meant to include all such possible diastereomers as well as their racemic and optically pure forms. Optically active (R) and (S), or (D) and (L), isomers may be prepared using chiral synthons or chiral reagents, or resolved using conventional techniques. When the compounds described herein contain olefinic double bonds or other centers of geometric asymmetry, unless specified otherwise, it is intended to include both E and Z geometric isomers. Likewise, all tautomeric forms are intended to be included.

The library of the present invention is useful as a screening tool for discovering new lead structures by evaluation across an array of biological assays, including the discovery of selective inhibition patterns across isozymes. The library is thus a tool for drug discovery; i.e., as a means to discover novel lead compounds by screening the library against a variety of biological targets and to develop structure-activity relationship (SAR) data in large families of related compounds. The library may be tested with the ligands attached to the solid supports as depicted in Formula I, or the compounds Z may be detached prior to evaluation. With the compounds of Formula I, screening assays such as FACS sorting and cell lawn assays may be used. A particularly useful lawn assay is described in U.S. patent application Ser. No. 08/553,056 (filed Nov. 3, 1995), the disclosure of which is incorporated herein by reference. When a compound is detached prior to evaluation, its relationship to its solid support is maintained, for example, by location within the grid of a standard 96-well plate or by location of activity on a lawn of cells. Whether the compounds are tested attached to or detached from the solid supports, the tags attached to the solid support associated with bioactivity may then be decoded to reveal the structural or synthetic history of the active compound (Ohlmeyer et al., *Proc. Natl. Acad. Sci. USA* 90, 10922–10926 (1993) and Still et al., Complex Combinatorial Chemical Libraries Encoded with Tags, WO 94/08051) or, alternatively, the structures may be determined by deconvolution. The usefulness of such a library as a screening tool is demonstrated by Burbaum et al., *Proc. Natl. Acad. Sci. USA* 92, 6027–6031(1995) who describe the assaying of encoded combinatorial libraries for, e.g., carbonic anhydrase inhibition. Even if no compounds are found to be active in a given screen, such lack of activity often provides useful SAR information.

In a lawn assay, a library of solid supports, preferably beads, is screened for the ability of compounds on the supports to affect the activity of an enzyme. Using the lawn assay, supports containing the active compounds are quickly and easily located merely by viewing zones of inhibition in a matrix. In one embodiment, the solid supports are contacted with a colloidal matrix such as agarose. The compounds are linked to the supports by a cleavable linker and released, e.g., by exposure to light. As they slowly diffuse out of the solid supports, zones of high concentration of the compounds are created in the supports' immediate vicinity. The compounds contact enzyme contained in the matrix. Substrate is contacted with the matrix and reacts with the enzyme. Conversion of substrate to product is measured by monitoring a photometric change in the substrate or in a coenzyme or cofactor involved in reaction. For example, the substrate can be fluorogenic, i.e., becoming fluorescent when converted to product. In this case, compounds that are active inhibitors of the enzyme reaction are detected as dark zones of inhibition. The less active, or inactive, compounds are contained in the lighter areas.

Using this assay, positive results from an assay of a combinatorial library can be detected very quickly. Furthermore, compound activity can be quantitated by, e.g., comparing the sizes of zones of activity. Once zones of activity have been determined, the relevant supports at the center of the zones can be located and the active compounds on those supports identified. The lawn assay thus allows large libraries of compounds to be quickly and easily screened. Very little effort is required to array the solid supports or assay the compounds released from the supports.

In another embodiment, the lawn assay is used to determine compounds that bind to a target molecule and thereby affect a detectable signal generated by a labeled compound bound to the target molecule. This assay allows screening of compounds that, e.g., act as agonists or antagonists of a receptor or that disrupt a protein-protein interaction. It also allows detection of binding to DNA, RNA or complex carbohydrates. For example, neurokinin receptor binds to a 7-nitrobenz-2-oxa-1,3-diazol-4-yl (NBD)—labeled peptide ligand. The labeled ligand has the following formula: PhCO—2,4-diaminobutyric acid(gamma-NBD)-Ala-D-Trp- Phe-D-Pro-Pro-NH2. NBD is a fluorophore and binding of the labeled ligand to the neurokinin receptor increases NBD's fluorescence. When a compound displaces the NBD-labeled ligand from the neurokinin receptor, fluorescence of the NBD fluorophore is reduced (G. Turcatti, H. Vogel, A. Chollet *Biochemistry* 34, 3972–3980 (1995)). A library of solid supports can be screened for compounds that bind to neurokinin receptor in a colloidal matrix using this method. Active compounds are found in zones of decreased fluorescence.

As another example, a radioligand (tritium or $^{125}$iodine-labeled) can be used to screen for compounds binding to a receptor with the lawn assay by using Scintillation Proximity Assay beads (SPA™, Amersham Corp.) or scintillant coated plates (Flashplates™, DuPont NEN Research Products). Receptor is bound to SPA™ beads or to a Flashplate™ surface, and radiolabeled ligand in a colloidal matrix is allowed to interact with the receptor. This interaction brings the radiolabel in close proximity with the scintillant and results in a scintillation signal. The signal can be detected using x-ray film, or other commercially available film that is specifically designed to detect tritium dependent scintillations. Compounds released into the matrix from the solid supports that bind to receptor and displace the radioligand reduce the scintillation signal, i.e., result in a zone of reduced scintillation. The receptor used in the assay can be, e.g., membrane-bound, tethered to a solid phase or solubilized.

When using the assay to find compounds that affect enzyme activity, it is advantageous to employ a substrate or product of the enzymatic reaction that generates a detectable signal. The difference in signal between the substrate and product should be significant. It is particularly preferred to use a substrate which generates little or no signal and which converts to a product which generates a strong signal. If the substrate produces detectable signal which cannot be distinguished from that of the product, it can create background noise, thereby reducing the overall sensitivity of the assay. For this reason, non-fluorescent substrates that convert to fluorescent products, i.e., fluorogenic substrates, are preferred. One well-known fluorogenic substrate is fluorescein diacetate, which converts to fluorescein in the presence of an esterase, such as carbonic anhydrase. Other fluorogenic substrates include 7-amino-trifluoromethyl coumarin (AFC), 4-trifluoromethylumbelliferyl (HFC), 7-amino-4-methylcoumarin (AMC) and 4-methoxy-2-naphthylamine (MNA).

Alternately, a fluorescent substrate can be used that converts to a product having different excitation and emission characteristics. By using band-pass filters so that only the product is excited and detected, the substrate can be effectively screened out. An example of such a fluorescent substrate is peptidylaminomethylcoumarin, which is converted by an appropriate protease such as thrombin, to free aminomethylcoumarin. The free aminomethylcoumarin excites and emits at different wavelengths than does the peptidylaminomethylcoumarin (S. Kawabata et al., *Eur. J. Biochem.* 172, 17 (1988)).

It is also possible to use a substrate containing internally quenched fluorophores that become fluorescent when converted to product. Such quenching reactions are well known (E. Matayushi et al., *Science* 247, 954 (1986)). For example, a peptide substrate can be produced having two fluorophores at opposite ends, one absorbing the fluorescence of the other. The substrate therefore emits a negligible amount of light. Upon cleavage of the peptide by a suitable protease, the absorbing fluorophore is released and no longer quenches the other fluorophore, resulting in an increase in fluorescence. In screening a library of aspartyl protease inhibitors using the lawn assay, those that are active inhibit cleavage of the substrate, allowing quenching to be maintained. Active compounds are found in dark zones of inhibition.

Fluorescence can be detected, e.g., using a field format fluorescence detection instrument such as Fluorimager™ from Molecular Dynamics. This type of fluorimeter is capable of determining fluorescence over a large area. It is also possible to detect fluorescence using a CCD camera and to transfer the image data to a computer. The image can be generated by illumination of the fluorophore with light of the wavelength that specifically excites it. Detection can be optimized by using a bandpass filter between the camera and the assay that is specific for the emission wavelength of the fluorophore.

Assays that measure a change in fluorescence are preferred as they are believed to result in the greatest sensitivity. Any method, however, can be used that measures a change in signal from one of the compounds involved in the reaction as a result of conversion of the substrate to product or displacement of the labeled ligand from the target. An example of an assay for compounds that affect a chromogenic substrate, p-nitrophenylphosphate, is described in the examples. It is also possible, for example, to measure a change in absorbance. For example, NADP is a common cofactor in many enzymatic reactions. Absorbance changes as NADPH is converted to NADP by, for example, neutrophil NADPH oxidase (such as during an oxidative burst associated with an immune response). This change can be monitored to determine zones of inhibition for compounds that inhibit this and other enzymes that use NADP, NADPH, NAD and NADH as co-factors. The sensitivity of assays that measure a change in absorbance is believed to be generally lower than those that measure a change in fluorescence.

Other examples of detectable changes resulting from conversion of substrate to product include chemiluminescent changes and scintillation changes. Scintillation changes can be detected as described above for receptor binding with the exception that a substrate is attached to the scintillant (i.e., to the bead or plate containing scintillant). For example, a radioactive reagent such as tritiated farnesyl pyrophosphate, can be added to the substrate by an enzyme such as farnesyl protein transferase. Transferase inhibitors prevent addition of the tritiated farnesyl pyrophosphate to the substrate, resulting in a reduction in detectable scintillations; i.e., transferase inhibitors are found in zones of reduced scintillation. In an alternative assay, removal of the radioactive portion of a substrate attached to the scintillant such as by cleaving with a protease, releases the radiolabeled portion (i.e., moves it away from the scintillant). In such an assay, protease inhibitors cause an increase in scintillation, i.e., are found in zones of increased scintillation. As noted above, the scintillation signal can be detected using x-ray film or film that is specifically designed to detect tritium dependent scintillations.

For assaying binding to a target molecule, a labeled ligand provides a signal that indicates such binding. The label is preferably a fluorescent moiety that alters its signal as a result of target molecule binding. Examples of such fluorescent moieties are NBD and 5-(dimethylamino)-1-naphthalenesulfonyl (Dansyl) chloride.

Colloidal matrices that are useful for the lawn assay include: silica gel; agar; agarose; pectin; polyacrylamide; gelatin; starch; gellan gum; cross-linked dextrans (such as Sephadex™, available from Supelco, Bellefonte Pa.); and any other matrix that allows diffusion of compound from the solid supports in a limited region. Low melting-temperature agarose is preferred, generally in an amount of 0.5–2.0%, wt./vol. The colloidal matrix can be chosen to obtain a desired rate of diffusion. It is generally preferred to use a matrix that allows a high concentration of compounds to be easily obtained.

In carrying out the assay to determine compounds that affect enzyme activity, the solid supports are preferably embedded in a matrix containing the relevant enzyme. Following cleavage, compound diffuses from the support into the matrix and contacts the enzyme. Substrate is then added and, as it diffuses into the colloidal matrix, active compounds inhibit conversion to product. By following such a procedure, compounds to be screened are allowed to interact with enzyme before the enzyme contacts substrate. This is believed to be advantageous because it allows compounds the best opportunity to inhibit the enzyme and thus results in the clearest zone of inhibition.

It is also possible, however, to embed the solid supports in a matrix that contains dispersed substrate. Following cleavage, the matrix can be contacted with enzyme. This procedure is not believed to be as sensitive since the compounds may not efficiently bind to the enzyme.

Solid supports can also be applied to the matrix's surface and the compounds allowed to diffuse into the matrix. This can be done, for example, by arraying the solid supports on the surface of a stretched sheet of plastic film (e.g., Parafilm™, available from Aldrich Co., Milwaukee, Wis.), and then applying the sheet to the surface of the matrix.

In assaying for compounds that affect enzyme activity, it may be desirable to use two colloidal matrices. For example, one matrix can contain enzyme and beads and the other can contain substrate. Contacting the surfaces of the matrices with each other allows the substrate to come into contact with the enzyme. It is also possible to add a solution of substrate over the surface of a matrix containing enzyme and embedded supports. Adding solution is preferred when, e.g., the substrate interferes with detection. Solution containing the substrate can be removed prior to determining the zones of activity.

When using the lawn assay to screen for binding to a target molecule, there is generally no need for more than one matrix. A matrix contains the target molecule bound to the labeled ligand which emits a detectable signal indicating binding to the target molecule. Compounds from the solid supports are diffused into the matrix, preferably from embedded supports using photolysis. Alternatively, however, labeled ligand can be diffused into the matrix from a second matrix (or liquid layer) after release of the compounds in the matrix. This allows the compounds to contact the receptor before interaction with the labeled ligand, which can be advantageous.

Compounds can be cleaved from the solid supports either before or after the supports are contacted with the colloidal matrix. For example, solid supports may contain acid cleavable linkers, as further described below. These linkers can be cleaved in a gaseous acidic atmosphere before placing the supports on the matrix. The compounds, although cleaved, remain on the surface of the supports and diffuse into the matrix when the supports are placed on it. It is even possible to cleave the compounds prior to pouring low-melt liquid agarose over the solid supports. While some of the compounds will be washed away, sufficient compound can remain on the support's surface to result in a recognizable zone of activity.

Where the compounds are cleaved after the beads are embedded in the colloidal matrix, it is preferred to use photolysis, e.g., cleaving by exposure to UV light. By adjusting light exposure, it is possible to control the amount of compound that diffuses into the matrix. If more light is applied, by increasing intensity or duration, more cleavage results, in turn releasing more compound into the matrix. This allows the amount of active compound released to be adjusted, so that zones of activity are only produced for compounds that are most active. The amount of compound released can also be optimized to produce zones that are most distinct.

The solid supports can be in a random arrangement, or in an ordered one. Preparing a random arrangement of solid supports requires little effort. For example, a library of beads can be suspended in a solvent, such as ethanol, and deposited on the bottom of a Petri plate. After the solvent has completely evaporated, a layer of agarose containing the relevant enzyme or target molecule can be poured over the beads. Alternatively, an ordered array can be used to space beads apart and allow easier identification of those that are active. In one example of an ordered array, beads are arrayed on a rigid template such as a thin glass disk having tapered holes. The tapered holes are sized to allow only single beads to settle into them. Beads are suspended in a solvent such as ethanol, and washed over the top of the template to fill each hole with one bead. The beads can then be cleaved in the dry state and the template set down on the colloidal matrix. Capillary action wets the beads, facilitating diffusion of the cleaved compounds into the matrix. Zones of activity can be observed immediately below beads containing active compounds. It is possible to remove the template prior to detecting zones of activity if an image of the template on the matrix is made. This image can later be used to correlate the zones of inhibition in the matrix with the positions of beads on the template.

Ordered arrays also may be useful in identifying the compounds on supports that are associated with zones of activity. Specifically, the array can be ordered so that the position of the solid support on the array corresponds to the identity of the compound. Thus, once an assay has been carried out and the position on the array determined for a support carrying an active compound, the identity of that compound can be easily determined.

Preferably, however, the identity of active compounds is determined using the encoding system described above, which employs tags T' encoding the identities of the compounds on the solid supports.

The assay is preferably carried out so that there is slow diffusion of the compound from the solid support following cleavage. This results in a high concentration of compound in the vicinity of the bead. Thus, very little compound is required to cause a distinct zone of activity. Most of the compound remains on the support for any subsequent assays that are required. Such further assays may be needed if more than one solid support is found in the zone of activity. It may then be necessary to retest the supports from the zone to determine which one releases the active compound. Reassaying may be required as a matter of course if many thousands of beads are screened at high density. Reassaying may also be desirable to test for selectivity, i.e. to determine which active compounds are inactive in a second assay that tests for a different property.

With combinatorial libraries containing thousands of related compounds, many compounds may be found that have some degree of activity. It therefore may be useful to use the lawn assay to distinguish the most potent compounds. In the assay, if the amount of compound released from each support is approximately the same, potent compounds have a detectable effect further from the bead than weak compounds do at any given time. Thus, the more active compounds create a larger zone of activity. Furthermore, the zone of activity of the most active compounds lasts longer. Thus, it is possible to quantify the activity of the compound eluted from the solid support by the size of the zone of activity as well as by the duration of the zone following cleavage.

Reducing photolysis time reduces the amount of compound released from the support. As the concentration of the compounds is lowered, those that are less active become more difficult to detect. As a result, the number of active compounds drops. In experiments described in the Examples that follow, compounds that were detectable at the shortest elution times, i.e., that were most potent, were also identified as most potent using conventional solution-phase screening. The activity of the inhibitors was found to correlate with the size and duration of the zone of activity: the most potent compounds produced the largest zones for the longest time for any given amount of photolysis.

When assaying a library containing many active compounds, it may be desirable to screen using a low density of solid supports, i.e., a low number of supports per $cm^3$ of matrix. While requiring more assays to screen the entire library, it is less likely that supports will have to be retested to determine which contains the active compound. Screening a large library containing many active members at a low density is often more efficient than screening at high density since rescreening supports is time consuming. The optimum density for screening can be determined for a given library by comparing the throughput in the initial assay with the effort required to retest active supports. Other factors which affect optimum screening density include the cost of the target and the size of the library.

When several large libraries are available for testing, it may be advantageous to incompletely evaluate each library by "scouting" each at high density for active compounds. Screening at high density allows one to statistically evaluate the number and potency of active compounds in each library. Libraries which contain the most active compounds can be more thoroughly tested.

If the proportion of active compounds screened in the assay is high, a second assay of the active compounds may be performed to choose those that should be further evaluated. The second assay can determine whether there is cross reactivity with other targets, i.e., a "selectivity screening." For example, a given library of compounds can be screened for activity against HIV protease, a member of the aspartyl protease family. Compounds found active in the initial assay can be counterscreened against a second, different aspartyl protease. Alternately, all compounds screened in the assay for activity against HIV protease could be simultaneously screened in the counter assay.

It is also possible to test for compounds that interfere with proteins that inhibit enzyme activity. In such an assay, the most active compounds prevent enzyme inhibition, resulting in more enzymatic catalysis. Thus, when a fluorogenic substrate is used, active compounds result in a brighter zone of activity. For example, P16 is a known protein inhibitor of cyclin-dependent kinase-4 (Cdk-4). Using the lawn assay, Cdk-4, Cyclin D1, P16, a fluorogenic substrate and a library of beads to be screened can be included in a layer of low-melt agarose. Following photocleavage and after allowing sufficient time to convert substrate to product, the gel can be subjected to an electrophoretic separation. Product migrates to the anode, where it is preferably trapped on an anode filter. The location of product on the filter indicates the position in the gel of compound that disrupts P16 inhibition of Cdk4.

In another embodiment of the lawn assay, an electrophoretic procedure is used to separate substrate from product to increase the sensitivity of the assay. In this embodiment, a substrate is used which changes charge when converted to product. Protein kinase A (PKA) phosphorylates a substrate having a net +1 charge, to form a phosphopeptide which has a net −1 charge. A lawn assay is performed in which PKA is contacted in a colloidal matrix with substrate and a library of potential inhibitors. An electrophoretic separation is then carried out across the width of (i.e., perpendicular to) the matrix. The phosphopeptide (i.e., product) moves towards the anode and the dephosphopeptide (i.e., substrate) moves towards the cathode. If a membrane is applied to one or both sides of the matrix during electrotransfer, electroblotting can be achieved. For example, the phosphopeptide can be electroblotted to a suitable membrane such as an Immobilon™ CD membrane.

Alternately, the dephosphopeptide can be electrotransferred to an appropriate paper such as Whatman™ 3MM paper. In another embodiment, the substrate and product can be chosen so that one is neutral and one is charged. Application of the electrophoretic field will remove the charged moiety. The resulting matrix will contain only the neutral moiety, thereby allowing detection of compounds that affect the conversion to product. The position of the bead containing the active compound can be determined by fluorescent imaging of the substrate or product using, e.g., photography or video imaging. This technique increases sensitivity of the lawn assay by separating fluorescent substrate from fluorescent product, concentrating the fluorescent image and by eliminating compounds from the matrix that might cause background signal. Other protein kinases and phosphatases such as protein kinase C, cyclin dependent kinases, MAP kinases and inositol monophosphatase can also be used with appropriate substrates in this method. A protease can also be screened by this method by using a substrate consisting of an appropriate peptide linked to a labeling moiety such as a fluorophore. The peptide sequence is selected so that the substrate and product will migrate differentially in an electric field.

Enzymes that can be used in the assay include, but are not limited to, the following:
Acid Phosphatase
Activated Protein C
Alkaline Phosphatase
Aminopeptidases B & M
Amyloid A4-Generating Enzyme
Angiotensinase
Aryl Sulfatase
β-Galactosidase
β-Glucosidase
β-Glucuronidase
Calpains I & II
Cathepsins B, C, D & G
Cholinesterase
Chymotrypsin
Collagenase
Dipeptidyl Peptidases I–IV
Elastase
Endothelin Converting Enzyme
Factor Xa
Factor XIa
Factor XIIa D$f$-Protease
Furin
γ-Glutamyltranspeptidase
Granzymes A & B
HIV Protease IL-1B Convertase
Kallikrein
Lysozyme
Mast Cell Protease
Peroxidase
Plasmepsin I and II
Plasmin
Prohormone Convertase
Γ ANP Precursor Processing Enzyme
Renin
Spleen Fibrinolytic Proteinase
Staphylocoagulase
Thrombin
Tissue Plasminogen Activator
Trypsin
Tryptase
Urokinase
Xanthine Oxidase The assay procedure is further illustrated by the Examples below.

EXAMPLES OF THE USE OF THE ASSAY

The lawn assay is performed in Petri plates using two layers of agarose, each about 1.5 mm thick. The first layer contains TentaGel S-NH$_2$™ beads (Rapp Polymere, Tubingen, Germany) and enzyme. The TentaGel S-NH$_2$™ beads have compounds to be screened attached thereto by a photocleavable linker and chemical tags attached for identifying the compounds, prepared according to methods described herein. The beads are either placed on the Petri plate and agarose poured over them or beads and agarose are first mixed and then poured together onto the plate. A second layer of agarose containing the fluorescein diacetate is contacted with the first layer to initiate the reaction.

More specifically: 50 mM sodium phosphate, pH 7.4, is used as a buffer and all solutions equilibrated in a 37° C. water bath immediately prior to initiation of the assay. 0.1 mL of 5.3 μM bovine carbonic anhydrase (Sigma Chemical Co.) is diluted in 2.15 mL of buffer and 1.25 mL of 2.5% low-gelling agarose added (Seaplaque™, FMC BioProducts). Library beads suspended in methanol are added to a 6 cm polystyrene Petri plate and, if necessary, distributed with a flat pipette tip. After evaporation of the methanol, the agarose solution is poured over the beads and allowed to gel at room temperature for 2–3 minutes. (Alternatively, dry beads can be added to a mixing tube and then enzyme and agarose added; the mixture is then centrifuged and poured.) The plate is then placed under a long wave (360 nm) UV lamp (Blackray™ UVP, Inc.) for from 5 seconds to 1 hour. After irradiation, 0.01 mL of fluorescein diacetate (10 mM in DMF, Molecular Probes, Eugene, Oreg.) is combined with 2.25 mL buffer and 1.25 mL of 2.5% agarose and poured over the first agarose layer. Detection is achieved by illumination using a short wavelength UV lamp (UVX, 254 nm) and image capture using a CCD camera coupled to a computer with NIH Image software obtained from the National Institutes of Health.

Fluorescein diacetate is hydrolyzed to produce fluorescein as the reaction proceeds. The plate then becomes significantly brighter except in the vicinity of beads that release inhibitors, thereby forming zones of inhibition. Beads at the center of these zones are removed with a hollow glass tube or a spatula and washed in methanol/methylene chloride (1:1) or with hot water (80° C.) to remove most of the agarose. After a final rinse in methanol, beads are either retested in a separate assay using the methods described above to confirm activity or analyzed to determine the relevant compound structures by tag decoding.

EXAMPLE 1

Assay of Two Known Inhibitors

In this example, two compounds were tested for inhibition of carbonic anhydrase by the lawn assay. Carbonic anhydrase inhibitors are useful in treating, e.g., glaucoma. Results were compared with those obtained using a conventional solution phase assay.

There is a high correlation shown between compounds that inhibit binding of dansylamide to carbonic anhydrase and those that inhibit conversion of fluorescein diacetate to fluorescein by carbonic anhydrase. This correlation is believed to result from dansylamide and fluorescein diacetate occupying the same active site (a zinc atom) on carbonic anhydrase. The solution phase assay measured inhibition of dansylamide binding. The lawn assay measured inhibition of the conversion of fluorescein diacetate to fluorescein.

Two aryl sulfonamide-containing compounds (compounds "A" and "B") were synthesized on TentaGel™ beads (Rapp Polymere) and assayed in the standard solution-phase assay and in the lawn assay. Compounds containing aryl sulfonamide substituents are known to be potent inhibitors of carbonic anhydrase. In the solution phase assay, $K_i$'s were determined to be 4 and 660 nM for compounds A and B respectively.

In the lawn assay, beads containing each compound were embedded in agarose in a series of Petri plates. The right side of each plate contained beads with compound A and the left side contained beads with compound B. Separate plates were irradiated for 2.5, 5, 10, 20 and 30 minutes. The more potent inhibitor of carbonic anhydrase (compound A) showed a clear zone of inhibition after only 2.5 minutes of photolysis. The weaker inhibitor (compound B) caused only a weak zone of inhibition after five minutes of photolysis. Ten minutes of photolysis was required to obtain a distinct zone. The clearest zones of inhibition were observed at the shortest time after photolysis. Zones at five minutes after photolysis were all sharper than at 15 minutes after photolysis. At 30 minutes after photolysis, all zones were much less distinct; some zones (for compound B) had disappeared.

In a second experiment, a plate containing beads with compounds A and B was irradiated for a predetermined period of time. The size and duration of the resulting zones of inhibition were determined. The zones resulting from compound A were larger than those resulting from compound B. Furthermore, the zones for compound A could be observed for a longer time. The signal from compound A persisted for more than two hours (although the zones became very diffuse) while signal for compound B all but disappeared after 90 minutes. In addition, zones of inhibition for compound A were more distinct, i.e., there was greater contrast between the zones and the surrounding areas.

EXAMPLE 2

Xanthine Oxidase Inhibition

The following materials are used:
3.9 μM hypoxanthine
0.3 mM 4-aminoantipyrene
2 mM 3,5-dichloro-2-hydroxybenzenesulfonate
50 mM sodium phosphate buffer, pH 7.5
5 U/mL horseradish peroxidase (Sigma P-6782, 5500 U/5 mg)
3 nM xanthine oxidase (buttermilk, Sigma X-4500, 16 U/mL) inhibitor Reactions are carried out in 24 μL total volume in 96-well U-bottom polypropylene microtiter dishes (Costar) containing the test compounds. Sodium phosphate buffer (8 μL, pH 7.5) is added to each well. A substrate mixture is prepared on ice by mixing 0.53 mL sodium phosphate buffer, 0.4 mL 4-aminoantipyrene (0.61 mg/mL), 0.4 mL 3,5-dichloro-2-hydroxybenzenesulfonate (5.3 mg/mL), 4 μL horseradish peroxidase (Sigma P-6782, 5500 U/5 mg), and 128 μL hypoxanthine 920 μg/mL. 8 μL of the substrate mixture is then transferred into each well. 8 μL xanthine oxidase (buttermilk, 9.0 nM, Sigma X-4500, 16 U/mL) in sodium phosphate buffer, pH 7.5 (or buffer alone as a control) is added last, directly into the reaction mixture. The plates are pulse-spun briefly in a tabletop centrifuge before reading absorbance. Absorbance is read using a dual kinetics program (490 minus 650 nm) for 15 min. at r.t. without automix in a microplate reader (Molecular Devices Thermomax). Initial rates are calculated (Vmax program) and compared to those of reactions without inhibitor.

Other examples of assay methods for evaluating the compounds of the present invention are disclosed in the following references which are incorporated herein by reference:

ACE Inhibition—Holmquist et al., "A Continuous Spectrophotometric Assay for Angiotensin Converting Enzyme", Anal. Biochem. 95, 540–548 (1979).

Thrombin Inhibition—Lottenberg et al., "Assay of Coagulation Proteases Using Peptide Chromogenic and Fluorogenic Substrates", Meth. in Enzymol. 80, 341–361 (1981).

Carbonic Anhydrase Inhibition—Maren and Couto, "The Nature of Anion Inhibition of Human Red Cell Carbonic Anhydrases", Archiv. of Biochem. and Biophys. 196, 501–510 (1979).

Carbonic Anhydrase Inhibition—Ponticelo et al., "Thienothiopyran-2-sulfonamides: A Novel Class of Water-Soluble Carbonic Anhydrase Inhibitors", J. Med. Chem. 30, 591–597 (1987).

Assays for evaluating the compounds of the present invention are well known in the art. Although the specific assays in which a particular library compound or group of library compounds will demonstrate activity are not known a priori, useful screening systems for assaying libraries of the format described herein have been developed. Biological assays for a wide variety of enzymes and molecule targets can identify activity among the entities of a combinatorial library.

Methods of Synthesis

The compounds of the present invention can be prepared according to the following methods. During each combinatorial step of the syntheses, each solid support upon which a compound is being synthesized is uniquely tagged to define the particular chemical event(s) occurring during that step. The tagging is accomplished using identifiers such as those of Formula II, which record the sequential events to which the support is exposed during the synthesis. Tagging thus provides a reaction history for the compound produced on each support. The identifiers are used in combination with one another to form a binary or higher order encoding scheme permitting a relatively small number of identifiers to encode a relatively large number of reaction products. For example, when used in a binary code, up to $2^{N-1}$ different compounds and/or conditions can be encoded. By associating each variable or combination of variables, at each combinatorial step of the synthesis with a combination of identifiers which uniquely define the chosen variables, such as reactant, reagent, reaction conditions, or combinations of these, one can use identifiers to define the reaction history of each solid support.

In carrying out the syntheses, one begins with at least $10^4$, desirably at least $10^7$, and generally not exceeding $10^{15}$ solid supports. Depending on the pre-determined number of $R^1$ choices for the first step, one divides the supports accordingly into as many containers. The appropriate reagents and reaction conditions are applied to each container and the combination of identifiers which encode for each $R^1$ choice is added and attached. The reagents are commercially available or are prepared by means well known in the art. Depending on the chemistries involved, the tagging may be done prior to, concomitantly with, or after the reactions which comprise each choice. As a control, a sample of the tagged supports can be taken at any stage during the reaction sequence and analyzed to obtain information about the synthesized compound. As needed, one may wash the beads free of any excess reagents or by-products before proceeding. At the end of each step, the supports are combined, mixed, and again divided, this time into as many containers as pre-determined for the number of $R^2$ choices for the second step in the synthesis. This procedure of dividing, reacting, tagging, and remixing is repeated until the combinatorial synthesis is completed (U.S. Pat. No. 5,663,046, issued Sep. 2, 1997).

Library Synthesis

Scheme 1

A. Coupling of Protected Lysine (2) to Resin (1).

A batch of amino-functionalized resin, such as PEG-grafted polystyrene beads (e.g. TentaGel™, 1) were modified with bis-Fmoc lysine, 2, to increase the available reaction sites for ligand attachment (Scheme 1). Bis-Fmoc lysine, 2, was coupled to amino-functionalized TentaGel, 1, by amide bond formation. Coupling was achieved by reacting a suspension of 1 in DMF with 2, HOBt and DIC. The suspension was shaken overnight, then drained or filtered and washed in succession with DMF, MeOH and DCM. The derivatized resin 3 so obtained was dried overnight under vacuum.

B. Tagging of Lysine loaded Resin (3)

The lysine loaded resin 3 was divided into a pre-determined number of reaction vessels for identification through tagging. In this instance, since fifteen amino-alcohols were used in the first combinatorial step, in fifteen reaction vessels were placed equal portions of resin. Identifiers were added prior to addition of the photo-labile linker and $R^1$ residues.

Unique tagging of the supports in each reaction vessel was achieved with combinations of additional identifiers encoded in a binary scheme for the subsequent fifteen choices of $R^1$. The identifiers were attached by adding a solution of up to two identifiers in DCM (in a 7.5–15% wt./wt. identifier:solid support ratio, depending on the signal strength of the identifier) to a batch of supports suspended in ethyl acetate or DCM, and shaking the mixture for 0.5–1 hour. A dilute solution of rhodium trifluoroacetate dimer was added and the mixture was immediately shaken overnight, then washed with DCM, MeOH and DCM. The procedure was repeated as necessary to add additional identifiers. For the purposes of simplicity, the identifiers were not shown in the schematics.

C. Attachment of Linker to Resin (4).

The Fmoc-protecting group on resin 3 was removed and 4-bromomethyl-3-nitrobenzoic acid (BNB) was attached. This was accomplished by the following method: A suspension of tagged resin 3 in 1:1 piperidine:DMF was shaken about 1.5 hr, then washed with DMF, MeOH, and DCM.

This diamine resin 4 was suspended in DMF, and treated with a solution of BNB, HOBt, and DIC in DMF. The suspension was shaken overnight, then drained and the resin was washed with DMF, MeOH, and DCM. The tagged BNB resin 5 was dried overnight in vacuo. This was repeated for each of the fifteen reaction vessels.

D. Attachment of Protected Amino Alcohols to Resin (5)

The fifteen batches of tagged BNB resin 5 were reacted with a unique, protected amino-alcohol (e.g., see Table 2-1) to generate resin-bound compound 6. The coupling of each amine occurred through displacement of the linker bromide and formation of a new carbon-nitrogen bond. Two cycles of reactions were performed to ensure complete conversion. In the first cycle, the amine was added to a suspension of resin 5 in THF and the mixture was shaken overnight. The mixture was drained and the resin was washed with THF. The THF solution containing the excess amine was then concentrated, taken up in DCM, washed with aqueous sodium bicarbonate, dried over sodium sulfate and concentrated. The residue was taken up in DMF and reacted with the same resin for the second reaction cycle. Lithium iodide was added to the suspension and the mixture was shaken overnight. The suspension was drained and the resin was washed with DMF, methanol, DCM and dried overnight in vacuo. This was repeated for each of the fifteen reaction vessels. After coupling, a small portion of each batch of resin was removed and titrated with picric acid to determine the extent of amine loading as a quality control for the reaction in this combinatorial step.

The protected amino alcohols were prepared directly from commercially available amino alcohols by silylation using TBS-Cl, TEA and DMAP in DCM according to the method of Baldwin et al. (*Tetrahedron* 50, 9411 (1994)). They were also obtained by reduction of the corresponding amino acids with borohydride and iodine in THF by the method of McKennon et al. (*J. Org. Chem.* 58, 3568 (1993)). The amino acids were commercially available.

The amines, 6, were pooled, mixed, and divided into a pre-determined number of reaction vessels. In this instance, since thirty-one acylating agents were used in the second combinatorial step, thirty-one reaction vessels were charged with equal portions of resin.

E. Coupling of Resin-linked Protected Amino Alcohol (6) with Carboxylic Acids The mixtures of amines, 6, were coupled with an acid corresponding to one of the thirty one $R^2$ choices in Table 2-2, by amide bond formation. This was accomplished by one of two procedures.

Procedure A: Each acid depicted in entries 1–27 was first converted to its acid chloride by standard conditions (oxalyl chloride, DCM, DMF, rt 2 hr). Each acid chloride was added to a suspension of amine resin 6 in pyridine. The mixture is shaken overnight, drained and the resin was washed with DMF, MeOH and DCM. This was repeated for the first twenty seven reaction vessels to afford the resin-linked protected β-hydroxy amide 7.

Procedure B: The remaining four reaction vessels containing the pooled amine 6 were all coupled with the same acid chloride 8, but after removal of the chloroacetyl protecting group, the resulting four mixtures of alcohols were each condensed with one of the four isocyanates in Table 2-3 to form carbamates. This was accomplished by the following method: The amine resin 6 was treated with acid chloride 8 in pyridine for 1.5 h. The resin was washed with DMF, methanol and DCM, and the chloroacetyl protecting group on 9 was cleaved by treatment with a solution of hydrazine in methanol for 1 hr. After washing of the resin with DMF, methanol and DCM, each mixture of alcohols, 10, was reacted with one of the isocyanates in Table 2-3. The isocyanate was added to a suspension of resin 10 in acetonitrile along with a catalytic amount of DBU. The mixture was shaken overnight, then drained and the resin was washed with DMF, methanol, DCM. The procedure was repeated for the four isocyanates to afford resin 11.

F. Tagging of Resin (7) and Resin (11)

Unique tagging of the supports in each reaction vessel was achieved with combinations of additional identifiers encoded in a binary scheme. The identifiers were attached by adding a solution of up to two identifiers in DCM (in a 7.5–15% wt./wt. identifier:solid support ratio, depending on the signal strength of the identifier) to a batch of supports suspended in ethyl acetate or DCM and shaking the mixture for 0.5–1 hr. A dilute solution of rhodium trifluoroacetate dimer was added and the mixture was immediately shaken overnight, then washed in DCM, MeOH, and DCM. The procedure was repeated as necessary to add additional identifiers.

Scheme 2

G. Deprotection and Oxidation of Resin (7) and Resin (11)

The resin was mixed and the conversion of the t-butyldimethylsilyl (TBS) ethers 7 and 11 to the corresponding aldehyde by deprotection and oxidation was accomplished on all the resin (Scheme 2). The protected alcohols, 7 and 11, were treated with dilute hydrochloric acid in methanol for 5–8 hr to remove the TBS protecting group. The resin was then washed with DMF, methanol and DCM. The resulting alcohols were oxidized to the corresponding aldehydes by the following method: To a suspension of the alcohol resin in DMSO was added a solution of IBX in DMSO and the mixture was shaken overnight. The suspension was drained, the resin was washed with DMSO and treated with another solution of IBX in DMSO for 4 hr. The mixture was then drained and the resin was washed with DMSO, methanol, DCM and dried overnight in vacuo.

H. Wittig Reaction of Resin (12) and Allyl Deprotection of Resin (13)

The resin bound aldehyde 12 was converted to an unsaturated ester 13 by a Wittig reaction. When 13 was an allyl ester, this was followed by allyl deprotection using morpholine and a catalytic amount of palladium(0) to provide acid 14. The resin bound aldehyde, 12, was suspended in THF and was reacted with a (triphenylphosphoranylidene) acetate ester overnight. After washing with THF, MeOH and DCM, the unsaturated ester 13 was obtained and dried in vacuo. When 13 was an allyl ester, it was suspended in DCM and catalytically deprotected by adding tetrakis (triphenylphosphine)palladium(0) and morpholine. The mixture was shaken overnight, drained and the resin was washed with pyridine, DMF, MeOH, and DCM, then dried overnight in vacuo to provide acid 14.

I. Formation of Active Ester of Resin (14) and Amine Addition

The mixture of resin bound acid 14 was divided into a pre-determined number of reaction vessels. In this instance, since twelve amines were used in the third combinatorial step, twelve reaction vessels were charged with equal portions of resin. In each flask, acid 14 was coupled with one of the amines in table 2-4, to provide the unsaturated amides 15 and 17. The resin was washed with DCM and DMF, then suspended in a small amount of 1:1 (v/v) DMF:pyridine. Pentafluorophenyl trifluoroacetate and pentafluorophenol were added. The mixture was shaken for 2 h at room temperature, drained, and washed with DMF. The resin bound PfP ester was then treated overnight with a solution of one of the amines from Table 2-4 in DMF. Unsaturated amides 15 and 17 were obtained after washing with DMF, MeOH, and DCM.

J. Formation of Acetate Ester of Resin (17)

Unsaturated amides containing free hydroxyl groups, 17, were protected as the corresponding acetates. Resin from the vessels containing amines 4, 5, and 6 (Table 2-4) were suspended in pyridine and treated with acetic anhydride and DMAP. After being shaken overnight, the protected alcohols, 18, were washed with DMF, methanol and DCM, then dried in vacuo.

Scheme 3

K. Formation of Hydroxyamides

Resins 13, 15, and 18, were then suspended in TFA (Scheme 3). After being shaken overnight, the resin was drained and washed with DCM and 1:9 (v/v) TEA in DCM. The resin was then immediately suspended in 1:9 (v/v) TEA in DCM. Following 5 h of shaking, the resin was drained and washed with DCM, MeOH, and DCM to provide the rearranged products, 19, 20, and 24, which were dried in vacuo. The acetate-protected amides, 20, were shaken for 2 h in a 1:9 (v/v) solution of hydrazine in methanol, to afford the resin bound product 22, which was washed with MeOH, DMF, MeOH and DCM, then dried overnight in vacuo.

The resultant resin batches were then tagged as described above or retained separately as sub-libraries. Amides of Formula III were obtained by cleavage of the resin-bound compounds, 19, 22, and 24, by exposing them to UV light (ca. 360 nM) for 15–180 minutes at 25–50° C. in a suitable solvent, such as methanol. This provided the free products, 21, 23, and 25, respectively.

PREPARATION AND USE OF IDENTIFIERS

Identifiers are of the general formula VIII:

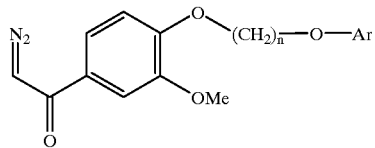

VIII wherein:

n=3–12 and Ar is pentachlorophenyl or n=3–6 and Ar is 2,4,6-trichlorophenyl. Eleven compounds of the general formula VIII were prepared (Ohlmeyer, M. H. J. et al., *Proc. Natl. Acad. Sci. USA* 90, 10922–10926 (1993); Burbaum, J. J. et al., *Proc. Natl. Acad. Sci. USA* 92, 6027–6031 (1995)).

In the synthesis of Example 1, identifiers were used to encode the combinatorial library. In Step 1, pentachlorophenyl identifiers where n=9–12 (abbreviated $C_9Cl_5$, $C_{10}Cl_5$, $C_{11}Cl_5$, and $C_{12}Cl_5$) were used in the following binary encoding scheme: 0001=(n=12), 0010=(n=11), 0100=(n=10) and 1000=(n=10). In Step 2, pentachlorophenyl identifiers where n=4–8 (abbreviated $C_4Cl_5$, $C_5Cl_5$, $C_6Cl_5$, $C_7Cl_5$, and $C_8Cl_5$) were used and encoded as follows: 00001=(n=8), 00010=(n=7), 00100=(n=6), 01000=(n=5), and 10000=(n=4).

EXAMPLE 1

5580 COMPOUND LIBRARY

Step 1 Sequential attachment of Bis-Fmoc lysine, photo-labile linker, amino alcohols ($R^1$), and encoding.

(1a) Attachment of bis-Fmoc lysine to TentaGel. Tentagel resin (1, S-NH$_2$, 12 g, 0.32 mmol/g, 3.84 mmol, 180–220 μm) was suspended in a DMF solution containing bis-Fmoc lysine (2, 11.2 mmol, 6.8 g) and HOBt (11.2 mmol, 1.5 g), then treated with DIC (22.4 mmol, 3.6 mL). The suspension was shaken overnight, then drained and washed with DMF, MeOH, and DCM. The resin 3 (Scheme 1) was then apportioned into fifteen reaction vessels.

(1b) Encoding of resin 3. For all the encoding steps, when one identifier was incorporated, an amount of reagent equal to 7.5% by mass of the resin to be encoded was used. When two identifiers were incorporated in the same step, an amount of reagent equal to 10% by mass of the resin to be encoded was used (Ohlmeyer, M. H. J. et al. *Proc. Natl. Acad. Sci. USA* 90, 10922–10926 (1993); Burbaum, J. J. et al. *Proc. Natl. Acad. Sci. USA* 92, 6027–6031(1995)).

Each of the fifteen batches in Step 1a were encoded prior to the addition of the photo-labile linker and the first combinatorial step with one or more of the $C_{12}Cl_5$-, $C_{11}Cl_5$-, $C_{10}Cl_5$- and $C_9Cl_5$ linker-diazoketones to produce the appropriate binary code. Identifiers were incorporated one or two at a time until the required binary code was completed. For example, resin batch 11 (12 g) was suspended in 100 mL of EtOAc, a solution of $C_{12}Cl_5$-linker-diazoketone (1.2 g) dissolved in 10 mL DCM was added followed by a solution of $C_{11}Cl_5$-linker-diazoketone (1.2 g) dissolved in 10 mL DCM. After agitation for 1 hr, rhodium trifluoroacetate dimer (10 mL of a 1.5 mg/mL solution in DCM) was added and the resin agitated at r.t. for a further 16 hr. The resin was then filtered and washed with DCM, MeOH, DCM and EtOAc. This resin batch was again suspended in 100 mL of EtOAc and a solution of $C_9Cl_5$-linker diazoketone (0.9 g) dissolved in 1 mL DCM was added. After agitation for 1 hr, rhodium trifluoroacetate dimer (10 mL of 1.5 mg/mL solution in DCM) was added and the resin was agitated at r.t. for a further 16 hr. The resin was then filtered and washed with DCM, MeOH, and DCM, then dried for 2 hr in vacuo.

(1c) Removal of Fmoc and attachment of photolinker. A suspension of tagged resin 3 (12 g) in 1:1 piperidine-DMF was shaken 1.5 hr, then drained and washed with DMF, MeOH, and DCM. This resin, 4, was suspended in DMF (40 mL), and treated with a pre-incubated (1 hr) solution of 4-bromomethyl-3-nitrobenzoic acid (BNB; 22.3 mmol, 5.8 g), HOBt (22.6 mmol, 3 g), and DIC (45.2 mmol, 7 mL) in DMF (60 mL). The suspension was shaken overnight, then drained and washed with DMF, MeOH, and DCM. This was repeated in tandem for each of the fifteen reaction vessels containing the tagged resin 3 to provide tagged resin 5.

(1d) Amino-alcohol addition. Each of the fifteen batches of resin was reacted with one of the TBS protected amino alcohols from Table 2-1. For example, a suspension of resin 5 (6 g) in THF (150 mL) was treated with TBS-phenylalaninol (2.95 g, 9.9 mmol) and shaken overnight. The resin was then drained and washed with THF. The filtrate was concentrated, the residue was taken up in DCM and washed with saturated aqueous sodium bicarbonate. The aqueous phase was extracted with DCM and the combined organic phase was dried over sodium sulfate and concentrated in vacuo. The residue was then added to a suspension of the same resin in DMF (120 mL) along with lithium iodide (3.7 mmol, 0.5 g). The mixture was shaken for 24 hr, drained and washed with DMF, MeOH, and DCM. This procedure was repeated in tandem, for each of the 15 amino alcohols in Table 2-1, then the resin was combined as a suspension in DCM, mixed to homogeneity and divided into 31 identical batches.

Step 2 Addition of $R^2$ acid chlorides and encoding.

The first twenty seven batches of resin 6 were each reacted with one of the acid chlorides derived from the acids in Table 2-2 (entries 1–27). The remaining four vessels were first reacted with the same acid chloride 8, then with hydrazine to remove the chloroacetate protecting group and finally each vessel was reacted with one of the four isocyanates in Table 2-3.

(2a) A suspension of resin 6 (1.67 g) in pyridine (10 mL) was treated with one of the twenty seven acid chlorides derived from the carboxylic acids shown in Table 2-2 (14.8 mmol). This suspension was shaken overnight, then drained and washed with DMF, MeOH, DMF, and DCM. This procedure was carried out in tandem for each of the twenty seven acid chlorides in Table 2-2 to provide acylated resin 7.

(2b) The four remaining batches of resin 6 (4×1.67g) were suspended in pyridine (4×10 mL) and reacted with acid chloride 8 (4×7.4 mmol, 4×1.3 mL). The four suspensions were shaken for 1.5 hr, drained and each washed with DMF, MeOH and DCM, giving 9. The four batches of resin 9 (4×1.67 g) were shaken 1 hr in a 10% hydrazine-MeOH (4×10 mL) solution, then drained and each washed with DMF, MeOH and DCM, thus providing 10. Each batch of resin 10 was treated with one of the isocyanates in table 2-3. To a suspension of the resin (4×1.67 g) in acetonitrile (10 mL) was added the isocyanate (14.8 mmol) along with a catalytic amount of DBU (30 μL). The mixture was shaken overnight, drained and the resin was washed with DMF, MeOH and DCM. This last procedure was carried out in tandem for each of the four isocyanates in Table 2-3 resulting in the formation of four batches of 11.

(2c) Each of the thirty-one resin batches in Step 2, 7 and 11, was encoded with one or more of the $C_8Cl_5$- through $C_4Cl_5$-linker-diazoketones to produce the appropriate binary code. Identifiers were incorporated one or two at a time until the required binary code was completed. For example, resin batch 13 (1.67 g) was suspended in 50 mL of EtOAc and a solution of $C_8Cl_5$-linker-diazoketone (0.13 g) dissolved in 5 mL DCM was added. After agitation for 1 hr, rhodium trifluoroacetate dimer (3.3 mL of a 1.5 mg/mL solution in DCM) was added and the resin agitated at r.t. for an additional 16 hr. The resin was then filtered and washed with DCM, MeOH, DCM and EtOAc. This resin batch was suspended in 50 mL of DCM and a solution of $C_6Cl_5$-linker diazoketone (0.18 g) dissolved in 5 mL DCM was added followed by a solution of $C_5Cl_5$-linker-diazoketone (0.18 g) dissolved in 5 mL DCM. After agitation for 1 hr, rhodium trifluoroacetate dimer (3.3 mL of 1.5 mg/mL solution in DCM) was added and the resin was agitated at r.t. for an additional 16 hr. The resin was then filtered and washed with DCM, MeOH, and DCM. After encoding, the thirty-one batches were combined as a suspension in DCM, mixed to homogeneity, filtered, and dried in vacuo.

Step 3 TBS Removal and conversion to the aldehyde.

(3a) The resin, 7 and 11, (10 g) was suspended in 150 mL of a 1% solution (v/v) of concentrated HCl in MeOH (Scheme 2). The mixture was shaken for 7 hr, drained and the resin was washed sequentially with MeOH, DMF, MeOH, and DCM.

(3b) The resin (10 g) was suspended in DMSO (130 mL) and a solution of IBX in DMSO (22.3 mmol, 20 mL of a 0.31 g/mL solution) was added. The mixture was shaken overnight, drained and the resin was washed with DMSO. The resin (10 g) was suspended in DMSO again and another solution of IBX (22.3 mmol, 20 mL of a 0.31 g/mL solution) was added. The mixture was shaken for 4 hr, drained, and the resin was washed with DMSO, MeOH, and DCM. The resin was dried overnight in vacuo providing 12.

Step 4 Wittig reaction and allyl deprotection.

(4a) The resin-bound aldehyde 12 (7 g) was suspended in THF, charged with a (triphenylphosphoranylidene) acetate ester (20 mmol) and shaken for 24 hours. The resin was then washed with THF, MeOH and DCM.

(4b) Allyl ester resin 13 (5.5 g) was suspended in DCM, charged with morpholine (1.1 mL, 12.6 mmol) and tetrakis(triphenylphosphine)palladium(0) (1.7 g, 1.5 mmol), then shaken for 1 hour. An additional portion of palladium (1.7 g, 1.5 mmol) was added and the reaction was allowed to continue for another hour. The resin was then washed with pyridine, DMF, MeOH and DCM. The resin was dried overnight in vacuo to give acid 14.

Step 5 Amide bond formation.

(5a) The acid 14 was divided into 12 reaction vessels, so that each vessel contained 0.43 grams of resin, then washed with DCM. In all 12 vessels, the resin (0.43 g) was suspended in DMF (2 mL). To this suspension pyridine (2 mL), pentafluorophenol (0.5 g, 2.7 mmol) and PfP trifluoroacetate (1 mL, 5.8 mmol) were added. The mixture was shaken for 2 hr, then drained and rinsed with DMF. In all 12 vessels, the resin was resuspended in DMF (6 mL), and to each vessel was added one of the amines in Table 2-4 (6 mmol). The mixture was shaken overnight, drained and the resin was washed with DMF, MeOH and DCM, resulting in the formation of amides 15 and 17. This procedure was carried out in tandem for each of the 12 amines in Table 2-4.

(5b) Next, amines from Table 2-4 containing free hydroxyl groups were protected. Three batches of resin 17 (3×0.43 g) were suspended in pyridine (3×4 mL) and acetic anhydride (3×2 mL, 21 mmol) was added along with a catalytic amount of DMAP. The mixture was shaken overnight, drained and washed with DMF, MeOH, and DCM, giving the protected compounds, 18.

Step 6 Rearrangement and deprotection.

(6a) Separately, ester resin 13 and diamide resins 15 and 18 (12×0.43 g) are suspended in trifluoroacetic acid (TFA) and shaken for 18 hours (Scheme 3). The resin is washed with DCM and 10% (v/v) TEA in DCM, then suspended in 10% (v/v) TEA in DCM and shaken for 5 hours. The resin is then drained and washed with MeOH, DCM, and MeOH and dried in vacuo, to provide the rearrangement products 19, 20, and 24.

(6b) The three vessels with protected alcohols were then deprotected. Resin 20 (3×0.43 g) was suspended in a 10% solution of hydrazine in methanol (3×10 mL), shaken for 2 hours, drained and washed with MeOH, DMF, MeOH, and DCM. Each of these final resin batches 21 was individually dried and stored as a separate sub-library, obviating any encoding for Step 5.

EXAMPLE 2

VERIFICATION OF SYNTHESIS

Several members from the library of Example 1 were synthesized on the solid phase to confirm the validity of the synthetic route and the identity of the final products. The compounds were cleaved from the resin via photoelution at 50° C. for 3–4 hr at 353 nm and the structures were confirmed by $^1$H NMR and mass spectroscopy.

EXAMPLE 3

DECODING PROCEDURE

The described decoding procedure was followed for the identification of selected compounds (Baldwin, J. J. et al., *J. Am. Chem. Soc.* 117, 5588–5589 (1995)). An encoded bead is transferred into a 1.3 mm diameter Pyrex capillary with 2 μL of acetonitrile. Ceric ammonium nitrate solution (2 μL of a 0.1 M aq. solution) and hexane (3 μL) are added and the two-phase mixture centrifuged briefly. The tube is sealed and left at 35° C. for 16 hr., then opened. The organic layer is removed by syringe and mixed with 1 μL of N,O-bis(trimethylsilyl)acetamide. The silated tag solution (1 μL) is analyzed by GC with electron capture (EC) detection.

The GC analysis is performed with a Hewlett Packard 5890 Plus gas chromatograph. On column injection into a 5 m, 0.32 mm retention gap connected to a 25 m, 0.2 mm crosslinked 5% phenylmethyl silicone column is used. The temperature and pressure programs for the analysis are: temperature ramp: 200–320° C. at 15° C./min., then 320° C. for 10 min.; and pressure ramp: 20–40 psi at 2 psi/min., then 40 psi for 10 min. The EC detector is maintained at 400° C. and the auxiliary gas is set at 35 psi.

The identity of the library compound attached to the bead is ascertained based on the reagents utilized in the synthesis of such compound, which are readily determined from the binary codes associated, respectively, with each of the identifiers for such reagents, as characterized through the above procedure.

EXAMPLE 4

FURTHER VERIFICATION OF SYNTHESIS AND TAGGING

Approximately two hundred beads from the library of Example 1 were randomly selected to confirm the validity of the synthetic route, the fidelity of the tags, and the identity of the final products. The beads were decoded according to Example 3, and the compounds were cleaved from the resin via photoelution at 50° C. for 3–4 h at 353 nm. Structures predicted by the decoding procedure were confirmed by mass spectroscopic analysis of the eluted products. These examples are listed in Table 3, where $R^1$, $R^2$ and $R^3$ represent pieces derived from the reagents listed in Tables 2-1, 2-2 and 2-4.

Scheme 1

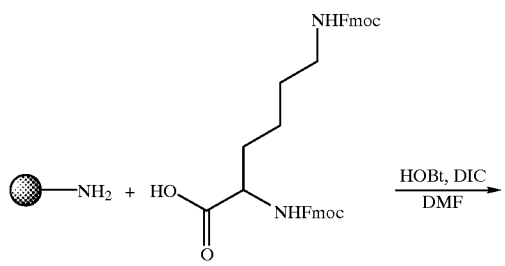

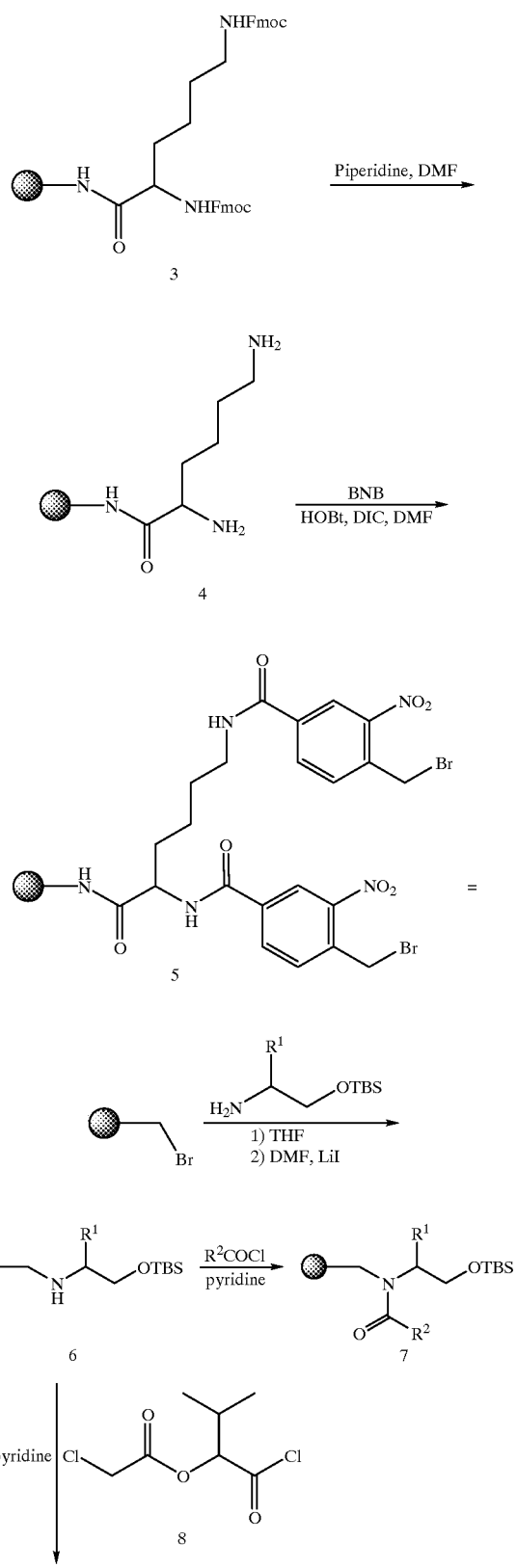

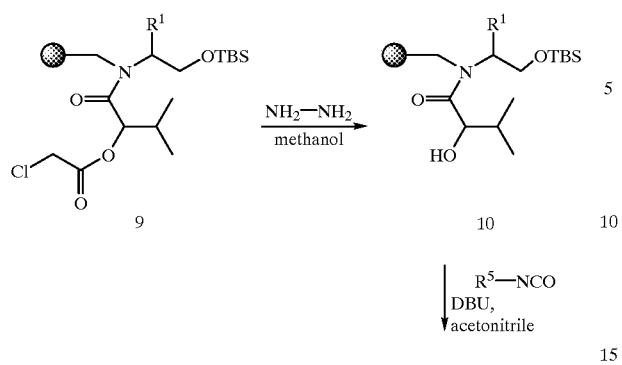
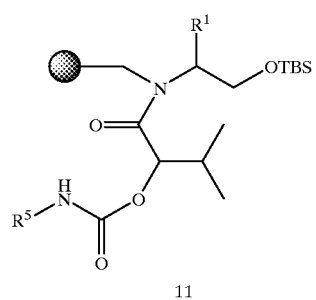
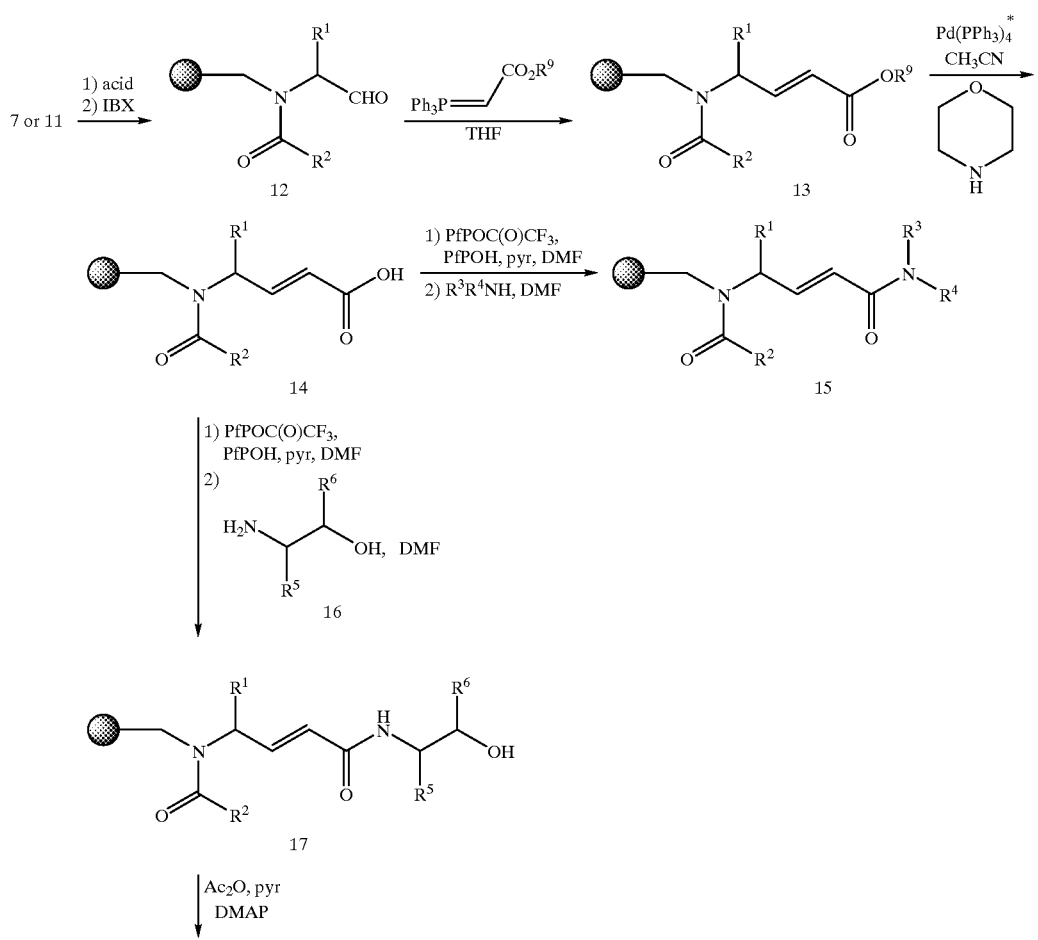
Scheme 2

-continued
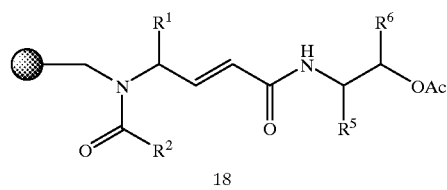
* When R⁹ is allyl.
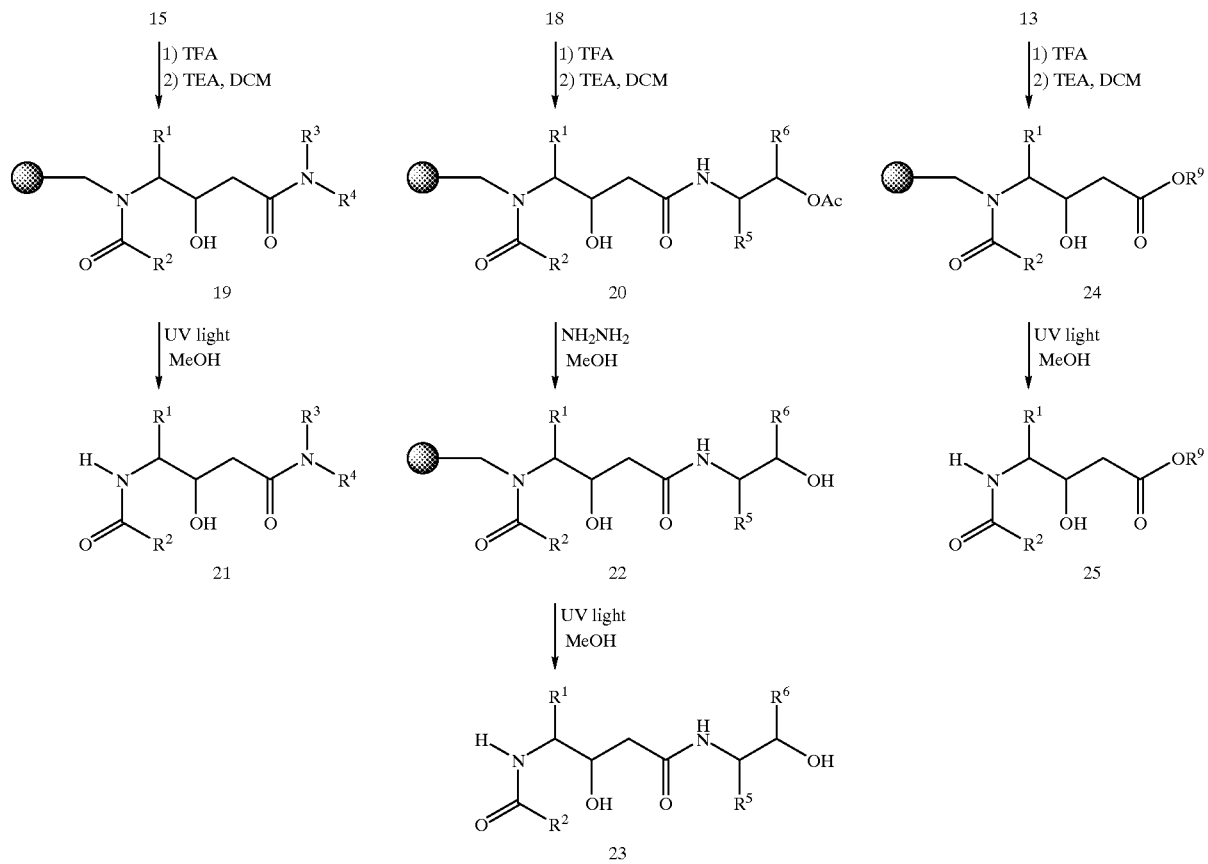

TABLE 1-continued

Linker Groups

| Linker Group -L' | Cleavage Conditions |
| --- | --- |
| (2-nitrobenzyl attached to B) | light |
| (alkoxy-substituted benzyl, RO- with B) | $Ce(NH_4)_2(NO_3)_6$ |
| (ortho-bromo benzyl with B) | Li, Mg or BuLi |
| -S-CH$_2$-B- | $Hg^{2+}$ |
| (X-substituted CH with CH$_2$-B) | Zn or Mg |
| (β-hydroxy alkyl -CH(OH)-CH$_2$-B) | Oxidation, e.g., $Pb(OAc)_4$ or $H_5IO_6$ |

R = H or lower alkyl; B = O or NH; and
X = electron withdrawing group such as Br, Cl and I.

⌇ = point of attachment to C(O).

TABLE 2-1

Amino Alcohol Reagents, (H$_2$N-CH(R$^1$)-CH$_2$-OTBS)

(HN-CH(R$^1$)-CH$_2$-OTBS)   (HN-CH(R$^1$)-CH$_2$-OTBS)

1. (benzyl amino alcohol, HN-CH(CH$_2$Ph)-CH$_2$-OTBS)
2. (n-butyl amino alcohol, HN-CH(n-Bu)-CH$_2$-OTBS)
8. (3,4-dichlorobenzyl amino alcohol, HN-CH(CH$_2$-3,4-Cl$_2$C$_6$H$_3$)-CH$_2$-OTBS)
9. (phenyl amino alcohol, HN-CH(Ph)-CH$_2$-OTBS)

TABLE 2-1-continued
Amino Alcohol Reagents,
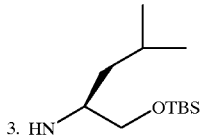

TABLE 2-1-continued

Amino Alcohol Reagents,

[Structure: H₂N-CH(R¹)-CH₂-OTBS]

[Structure: HN(R¹-containing)-OTBS]  [Structure: HN(R¹-containing)-OTBS]

15. [Structure: HN-(CH₂)₄-CH(CH₂OTBS)- with NHAc group]

TABLE 2-2

Carboxylic Acid Reagents (R²CO₂H)

R²C(O)—  R²C(O)—

1. 4-chlorophenoxyacetone derivative 8. 2-acetylfuran 2. 5-methyl-2-hexanone derivative 9. acetophenone 3. 4,4-dimethyl-2-pentanone derivative 10. 4-acetylbiphenyl 4. 4-cyclopentyl-2-butanone derivative 11. 4'-butoxyacetophenone derivative TABLE 2-2-continued
| Carboxylic Acid Reagents (R²CO₂H) | |
|---|---|
| R²C(O)— | R²C(O)— |
| 5. 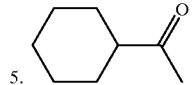 | 12. 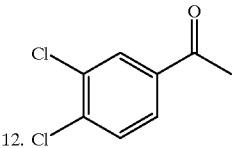 |
| 6. 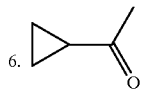 | 13. 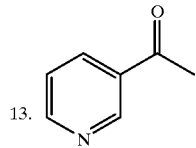 |
| 7. 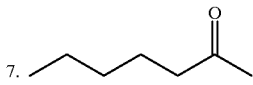 | 14. 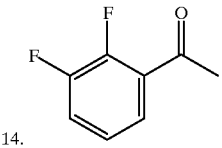 |
| 15. 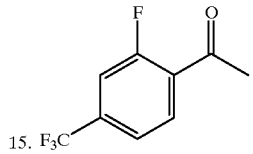 | 22. 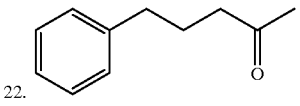 |
| 16. 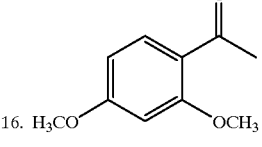 | 23. 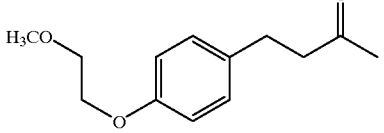 |
| 17. 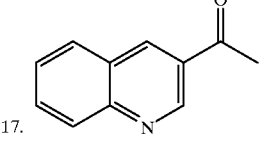 | 24. 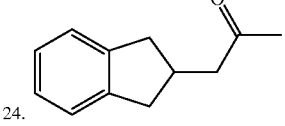 |
| 18. 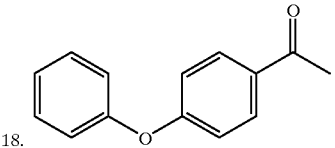 | 25. 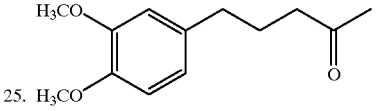 |
| 19. 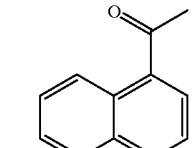 | 26. 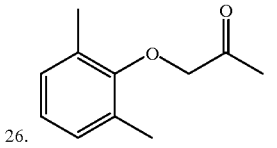 |

TABLE 2-2-continued

Carboxylic Acid Reagents (R²CO₂H)

| R²C(O)— | R²C(O)— |
|---|---|
| 20. 1,1-diphenyl-butan-2-one acyl group | 27. 1-(naphthalen-2-yloxy)propan-2-one acyl group |
| 21. N-Cbz-prolinyl methyl ketone acyl group | 28. Bu-NH-C(O)-O-CH(iPr)-C(O)- |
| 29. p-(PhO)Ph-NH-C(O)-O-CH(iPr)-C(O)- | |
| 30. Ph-NH-C(O)-O-CH(iPr)-C(O)- | |
| 31. Ph(CH₂)₂-NH-C(O)-O-CH(iPr)-C(O)- | |

TABLE 2-3

Isocyanate Reagents (R⁵NCO)

| Isocyanate Reagent |
|---|
| 1. n-Bu-NCO (propyl isocyanate) |
| 2. 4-phenoxyphenyl isocyanate |
| 3. phenyl isocyanate |
| 4. phenethyl isocyanate |

TABLE 2-4

Amine Reagents (R⁴R³NH)

R⁴R³N—

1. HN-butyl (n-butylamine)
2. HN-CH(CH₃)-C(O)-NH-butyl (alaninamide derivative)
3. HN-CH(CH₃)-C(O)-NH-CH(CH₂CH(CH₃)₂)-C(O)-NH₂ (dipeptide)

R⁴R³N—

8. HN-(3S)-pyrrolidinyl-N-benzyl
9. 1-methylpiperazine (N-methylpiperazine)
10. 1-methylpiperidine-3-carboxamide TABLE 2-4-continued Amine Reagents (R⁴R³NH)

R⁴R³N—

5. HN-CH(Ph)-CH(Ph)-OH (diphenyl amino alcohol, one stereoisomer)
6. HN-CH(Ph)-CH(Ph)-OH (diphenyl amino alcohol, other stereoisomer)
7. HN-(CH₂)₃-imidazol-1-yl

R⁴R³N—

12. HN-CH₂-(1H-benzimidazol-2-yl)

TABLE 2-5

Wittig Ester (Ph₃P=CHCO₂R⁹)

=CHCO₂R⁹

1. =CHC(O)-O-CH₂CH₃
4. =CHC(O)-O-CH₂CH₂CH₃

=CHCO₂R⁹

2. =CHC(O)-O-CH₂-CH=CH₂
5. =CHC(O)-O-CH₂CH₂CH₂CH₃

=CHCO₂R⁹

3. =CHC(O)-O-CH₂-phenyl

TABLE 2-4-continued

Amine Reagents (R⁴R³NH)

R⁴R³N—

4. HN-CH(CH₂Ph)-CH₂OH

R⁴R³N—

11. 4-(N-benzyl)piperidinyl-amine (1-benzyl-piperidin-4-yl-amine)

TABLE 3

Single Bead Mass Spectrometry Data

| Example Number | R¹ (Table 2-1) | R² (Table 2-2) | R³, R⁴ (Table 2-4) | Expected MW | Observed MW | Ion Type |
|---|---|---|---|---|---|---|
| 1 | 6 | 1 | 1 | 463.02 | 463.4 | M+ |
| 2 | 10 | 1 | 1 | 447.02 | 447.4 | M+ |
| 3 | 1 | 20 | 1 | 472.68 | 473.3 | MH+ |
| 4 | 15 | 9 | 1 | 391.57 | 392.5 | MH+ |
| 5 | 3 | 7 | 1 | 328.56 | 329.2 | MH+ |
| 6 | 6 | 14 | 1 | 434.53 | 435.3 | MH+ |
| 7 | 1 | 3 | 1 | 362.57 | 363.4 | MH+ |
| 8 | 3 | 8 | 1 | 324.47 | 325.6 | MH+ |
| 9 | 6 | 11 | 1 | 470.67 | 471.4 | MH+ |
| 10 | 10 | 8 | 1 | 372.51 | 373.5 | MH+ |
| 11 | 3 | 31 | 1 | 477.72 | 478.3 | MH+ |
| 12 | 8 | 19 | 1 | 487.46 | 487.4 | M+ |

TABLE 3-continued

Single Bead Mass Spectrometry Data

| Example Number | R¹ (Table 2-1) | R² (Table 2-2) | R³, R⁴ (Table 2-4) | Expected MW | Observed MW | Ion Type |
|---|---|---|---|---|---|---|
| 13 | 8 | 4 | 1 | 457.49 | 457.3 | M+ |
| 14 | 3 | 22 | 1 | 376.60 | 377.3 | MH+ |
| 15 | 6 | 19 | 1 | 448.61 | 449.3 | MH+ |
| 16 | 1 | 29 | 1 | 575.77 | 576.5 | MH+ |
| 17 | 12 | 2 | 1 | 438.67 | 439.2 | MH+ |
| 18 | 12 | 20 | 1 | 548.78 | 549.2 | MH+ |
| 19 | 12 | 19 | 1 | 494.68 | 495.4 | MH+ |
| 20 | 15 | 31 | 2 | 605.87 | 606.2 | MH+ |
| 21 | 3 | 29 | 2 | 612.85 | 613.2 | MH+ |
| 22 | 2 | 9 | 2 | 405.60 | 406.3 | MH+ |
| 23 | 8 | 16 | 2 | 568.55 | 568.3 | M+ |
| 24 | 8 | 27 | 2 | 588.58 | 588.3 | M+ |
| 25 | 5 | 16 | 2 | 451.63 | 452.4 | MH+ |
| 26 | 1 | 15 | 2 | 525.60 | 526.3 | MH+ |
| 27 | 9 | 7 | 2 | 419.63 | 419.4 | M+ |
| 28 | 4 | 2 | 2 | 357.56 | 358.3 | MH+ |
| 29 | 5 | 14 | 2 | 427.55 | 428.4 | MH+ |
| 30 | 8 | 17 | 2 | 559.54 | 559.4 | M+ |
| 31 | 8 | 8 | 2 | 498.45 | 498.2 | M+ |
| 32 | 12 | 18 | 2 | 607.81 | 608.3 | MH+ |
| 33 | 13 | 7 | 2 | 483.72 | 484.2 | MH+ |
| 34 | 5 | 4 | 2 | 411.66 | 412.2 | MH+ |
| 35 | 4 | 17 | 2 | 414.56 | 414.7 | M+ |
| 36 | 2 | 1 | 2 | 470.07 | 470.2 | M+ |
| 37 | 10 | 18 | 2 | 545.74 | 546.2 | MH+ |
| 38 | 15 | 31 | 2 | 605.87 | 606.5 | MH+ |
| 39 | 3 | 14 | 3 | 498.64 | 499.3 | MH+ |
| 40 | 7 | 28 | 3 | 626.28 | 628.2 | MH+ |
| 41 | 15 | 22 | 3 | 561.81 | 562.2 | MH+ |
| 42 | 12 | 19 | 3 | 622.83 | 623.2 | MH+ |
| 43 | 9 | 12 | 3 | 551.52 | 551.5 | M+ |
| 44 | 1 | 17 | 3 | 547.72 | 548.3 | MH+ |
| 45 | 2 | 8 | 3 | 452.62 | 453.2 | MH+ |
| 46 | 1 | 10 | 3 | 572.77 | 573.2 | MH+ |
| 47 | 3 | 14 | 3 | 498.64 | 499.4 | MH+ |
| 48 | 6 | 29 | 3 | 733.95 | 735.1 | MH+ |
| 49 | 7 | 9 | 3 | 531.11 | 531.3 | M+ |
| 50 | 4 | 6 | 3 | 384.54 | 385.3 | MH+ |
| 51 | 14 | 4 | 3 | 522.82 | 523.2 | MH+ |
| 52 | 2 | 11 | 3 | 534.78 | 535.2 | MH+ |
| 53 | 12 | 20 | 3 | 676.93 | 677.2 | MH+ |
| 54 | 12 | 9 | 3 | 572.77 | 573.2 | MH+ |
| 55 | 15 | 15 | 3 | 605.71 | 628.2 | M+ Na |
| 56 | 14 | 27 | 3 | 582.82 | 583.3 | MH+ |
| 57 | 7 | 8 | 3 | 521.07 | 521.2 | M+ |
| 58 | 14 | 5 | 4 | 458.71 | 459.3 | MH+ |
| 59 | 7 | 27 | 4 | 561.12 | 561.4 | M+ |
| 60 | 10 | 21 | 4 | 587.78 | 588.3 | MH+ |
| 61 | 5 | 20 | 4 | 502.71 | 503.2 | MH+ |
| 62 | 14 | 19 | 4 | 502.71 | 503.3 | MH+ |
| 63 | 7 | 28 | 4 | 576.20 | 576.3 | M+ |
| 64 | 1 | 8 | 4 | 436.55 | 437.3 | MH+ |
| 65 | 6 | 7 | 4 | 470.67 | 471.3 | MH+ |
| 66 | 8 | 18 | 4 | 607.57 | 608.4 | MH+ |
| 67 | 11 | 29 | 4 | 729.94 | 730.3 | MH+ |
| 68 | 10 | 18 | 4 | 552.72 | 553.3 | MH+ |
| 69 | 2 | 8 | 4 | 402.54 | 403.4 | MH+ |
| 70 | 15 | 20 | 4 | 573.80 | 574.2 | MH+ |
| 71 | 8 | 10 | 4 | 591.57 | 591.3 | M+ |
| 72 | 9 | 1 | 4 | 497.03 | 497.4 | M+ |
| 73 | 8 | 31 | 4 | 658.68 | 658.2 | M+ |
| 74 | 14 | 27 | 5 | 594.81 | 595.2 | MH+ |
| 75 | 10 | 15 | 5 | 608.68 | 609.2 | MH+ |
| 76 | 8 | 27 | 5 | 657.63 | 657.2 | M+ |
| 77 | 10 | 6 | 5 | 486.66 | 487.2 | MH+ |
| 78 | 15 | 7 | 5 | 525.76 | 526.5 | MH+ |
| 79 | 5 | 22 | 5 | 502.71 | 503.2 | MH+ |
| 80 | 10 | 1 | 5 | 587.16 | 587.2 | M+ |
| 81 | 8 | 7 | 5 | 571.59 | 571.2 | M+ |
| 82 | 13 | 16 | 5 | 618.78 | 619.2 | MH+ |
| 83 | 10 | 26 | 5 | 580.78 | 581.2 | MH+ |
| 84 | 11 | 31 | 5 | 727.97 | 728.2 | MH+ |
| 85 | 11 | 4 | 5 | 604.85 | 605.2 | MH+ |
| 86 | 10 | 15 | 5 | 608.68 | 609.3 | MH+ |
| 87 | 14 | 1 | 5 | 579.19 | 579.2 | M+ |
| 88 | 2 | 20 | 5 | 578.81 | 579.2 | MH+ |
| 89 | 3 | 2 | 6 | 468.70 | 469.2 | MH+ |
| 90 | 11 | 19 | 6 | 634.82 | 635.2 | MH+ |
| 91 | 5 | 28 | 6 | 555.79 | 556.3 | MH+ |
| 92 | 7 | 28 | 6 | 638.27 | 638.2 | M+ |
| 93 | 14 | 25 | 6 | 616.87 | 617.2 | MH+ |
| 94 | 2 | 7 | 6 | 468.70 | 469.2 | MH+ |
| 95 | 9 | 13 | 6 | 495.62 | 496.3 | MH+ |
| 96 | 12 | 23 | 6 | 686.91 | 687.2 | M+ |
| 97 | 8 | 15 | 6 | 663.53 | 664.8 | MH+ |
| 98 | 10 | 23 | 6 | 624.84 | 625.3 | MH+ |
| 99 | 3 | 23 | 6 | 576.80 | 577.2 | MH+ |
| 100 | 13 | 2 | 6 | 552.77 | 553.2 | MH+ |
| 101 | 6 | 29 | 6 | 745.94 | 746.6 | MH+ |
| 102 | 7 | 9 | 6 | 543.10 | 543.2 | M+ |
| 103 | 3 | 27 | 6 | 554.74 | 555.2 | MH+ |
| 104 | 8 | 5 | 6 | 583.60 | 583.2 | M+ |
| 105 | 14 | 9 | 7 | 426.62 | 427.4 | MH+ |
| 106 | 3 | 5 | 7 | 392.61 | 393.4 | MH+ |
| 107 | 14 | 3 | 7 | 420.67 | 421.4 | MH+ |
| 108 | 10 | 20 | 7 | 538.75 | 539.4 | MH+ |
| 109 | 13 | 8 | 7 | 460.58 | 461.4 | MH+ |
| 110 | 14 | 11 | 7 | 498.74 | 499.5 | MH+ |
| 111 | 7 | 5 | 7 | 461.06 | 461.4 | M+ |
| 112 | 15 | 4 | 7 | 463.70 | 464.5 | MH+ |
| 113 | 4 | 28 | 7 | 439.63 | 440.4 | MH+ |
| 114 | 12 | 8 | 7 | 486.62 | 487.3 | MH+ |
| 115 | 12 | 9 | 7 | 496.66 | 497.4 | MH+ |
| 116 | 13 | 2 | 7 | 464.67 | 465.3 | MH+ |
| 117 | 10 | 19 | 7 | 484.65 | 485.4 | MH+ |
| 118 | 12 | 16 | 7 | 556.72 | 557.3 | MH+ |
| 119 | 2 | 26 | 7 | 444.64 | 445.4 | MH+ |
| 120 | 5 | 6 | 7 | 336.49 | 337.4 | MH+ |
| 121 | 15 | 28 | 7 | 538.78 | 539.4 | MH+ |
| 122 | 2 | 26 | 8 | 495.73 | 496.5 | MH+ |
| 123 | 4 | 3 | 8 | 389.60 | 390.4 | MH+ |
| 124 | 8 | 3 | 8 | 534.58 | 534.4 | M+ |
| 125 | 1 | 27 | 8 | 551.74 | 552.5 | MH+ |
| 126 | 4 | 3 | 8 | 389.60 | 390.4 | MH+ |
| 127 | 14 | 10 | 8 | 553.81 | 554.4 | MH+ |
| 128 | 10 | 25 | 8 | 587.83 | 588.4 | MH+ |
| 129 | 7 | 21 | 8 | 633.25 | 633.3 | M+ |
| 130 | 9 | 2 | 8 | 451.67 | 451.5 | M+ |
| 131 | 11 | 20 | 8 | 651.91 | 652.4 | MH+ |
| 132 | 14 | 30 | 8 | 592.86 | 593.6 | MH+ |
| 133 | 7 | 19 | 8 | 556.15 | 556.3 | M+ |
| 134 | 4 | 5 | 9 | 325.51 | 326.4 | MH+ |
| 135 | 5 | 7 | 9 | 341.56 | 342.4 | MH+ |
| 136 | 6 | 8 | 9 | 415.54 | 416.3 | MH+ |
| 137 | 4 | 9 | 9 | 319.45 | 320.4 | MH+ |
| 138 | 15 | 19 | 9 | 468.66 | 469.5 | MH+ |
| 139 | 2 | 30 | 9 | 476.69 | 477.4 | MH+ |
| 140 | 12 | 28 | 9 | 566.82 | 567.4 | MH+ |
| 141 | 1 | 3 | 9 | 389.60 | 390.4 | MH+ |
| 142 | 5 | 29 | 9 | 554.76 | 555.3 | MH+ |
| 143 | 8 | 19 | 9 | 514.49 | 514.3 | M+ |
| 144 | 13 | 31 | 9 | 588.82 | 589.4 | MH+ |
| 145 | 1 | 8 | 9 | 385.51 | 386.4 | MH+ |
| 146 | 3 | 18 | 9 | 453.64 | 454.3 | MH+ |
| 147 | 10 | 26 | 9 | 467.67 | 468.3 | MH+ |
| 148 | 13 | 26 | 9 | 503.70 | 504.3 | MH+ |
| 149 | 5 | 15 | 9 | 433.50 | 434.3 | MH+ |
| 150 | 6 | 30 | 9 | 540.73 | 541.3 | MH+ |
| 151 | 2 | 17 | 9 | 412.59 | 413.4 | MH+ |
| 152 | 14 | 26 | 9 | 459.70 | 460.4 | MH+ |
| 153 | 2 | 8 | 10 | 379.51 | 380.3 | MH+ |
| 154 | 15 | 18 | 10 | 538.71 | 539.3 | MH+ |
| 155 | 11 | 11 | 10 | 571.78 | 572.3 | MH+ |
| 156 | 3 | 29 | 10 | 596.80 | 597.4 | MH+ |
| 157 | 12 | 16 | 10 | 559.72 | 560.3 | MH+ |
| 158 | 14 | 2 | 10 | 423.67 | 424.3 | MH+ |

TABLE 3-continued

Single Bead Mass Spectrometry Data

| Example Number | R¹ (Table 2-1) | R² (Table 2-2) | R³, R⁴ (Table 2-4) | Expected MW | Observed MW | Ion Type |
|---|---|---|---|---|---|---|
| 159 | 2 | 31 | 10 | 532.76 | 533.4 | MH+ |
| 160 | 6 | 5 | 10 | 459.65 | 460.3 | MH+ |
| 161 | 1 | 18 | 10 | 515.66 | 516.2 | MH+ |
| 162 | 15 | 26 | 10 | 504.70 | 505.3 | MH+ |
| 163 | 14 | 28 | 10 | 524.79 | 525.3 | MH+ |
| 164 | 15 | 6 | 10 | 410.58 | 411.4 | MH+ |
| 165 | 5 | 1 | 10 | 439.99 | 440.3 | MH+ |
| 166 | 5 | 30 | 10 | 490.67 | 491.4 | MH+ |
| 167 | 4 | 2 | 10 | 341.51 | 342.3 | MH+ |
| 168 | 7 | 28 | 10 | 553.17 | 553.3 | M+ |
| 169 | 7 | 20 | 10 | 562.16 | 562.2 | M+ |
| 170 | 6 | 2 | 10 | 447.64 | 448.2 | MH+ |
| 171 | 12 | 10 | 10 | 575.76 | 576.3 | MH+ |
| 172 | 2 | 19 | 11 | 501.73 | 502.4 | MH+ |
| 173 | 8 | 23 | 11 | 656.71 | 656.4 | M+ |
| 174 | 11 | 8 | 11 | 551.74 | 552.4 | MH+ |
| 175 | 8 | 28 | 11 | 649.73 | 649.4 | M+ |
| 176 | 15 | 21 | 11 | 635.89 | 636.6 | MH+ |
| 177 | 3 | 25 | 11 | 553.82 | 554.4 | MH+ |
| 178 | 2 | 28 | 11 | 546.84 | 547.4 | MH+ |
| 179 | 2 | 2 | 11 | 445.72 | 446.4 | MH+ |
| 180 | 10 | 29 | 11 | 706.96 | 707.5 | MH+ |
| 181 | 6 | 2 | 11 | 509.76 | 510.4 | MH+ |
| 182 | 11 | 29 | 11 | 769.03 | 769.5 | M+ |
| 183 | 4 | 20 | 11 | 513.74 | 514.4 | MH+ |
| 184 | 15 | 6 | 11 | 472.70 | 473.5 | MH+ |
| 185 | 15 | 8 | 11 | 498.69 | 499.5 | MH+ |
| 186 | 12 | 10 | 11 | 637.88 | 638.4 | MH+ |
| 187 | 11 | 23 | 11 | 663.93 | 664.4 | MH+ |
| 188 | 5 | 26 | 11 | 495.73 | 496.5 | MH+ |
| 189 | 8 | 17 | 11 | 605.61 | 628.2 | M+ Na |
| 190 | 2 | 1 | 12 | 473.02 | 473.3 | M+ |
| 191 | 11 | 10 | 12 | 594.76 | 595.3 | MH+ |
| 192 | 12 | 24 | 12 | 572.76 | 573.3 | MH+ |
| 193 | 5 | 19 | 12 | 444.58 | 445.3 | MH+ |
| 194 | 2 | 16 | 12 | 468.61 | 469.2 | MH+ |
| 195 | 13 | 29 | 12 | 699.87 | 700.4 | MH+ |
| 196 | 12 | 17 | 12 | 569.71 | 570.3 | MH+ |
| 197 | 6 | 19 | 12 | 522.65 | 523.3 | MH+ |
| 198 | 8 | 4 | 12 | 531.53 | 531.3 | M+ |
| 199 | 8 | 11 | 12 | 583.56 | 583.4 | M+ |
| 200 | 7 | 10 | 12 | 553.10 | 553.2 | M+ |
| 201 | 14 | 6 | 12 | 412.59 | 413.4 | MH+ |
| 202 | 3 | 5 | 12 | 414.61 | 414.3 | M+ |
| 203 | 10 | 6 | 12 | 420.56 | 421.3 | MH+ |
| 204 | 1 | 18 | 12 | 534.66 | 535.2 | MH+ |

We claim:

1. A combinatorial chemical library for biological assay comprising a plurality of members of the Formula I:

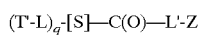

wherein:

T is a tag;

L is a first linker;

T-L- together form an identifier residue;

q is 0–30;

[S] is a solid support;

-L' is a second linker;

-Z is a compound of formula

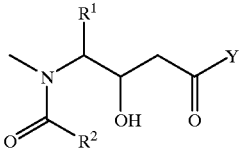

wherein:
R¹ is chosen from the group consisting of alkyl, aralkyl, aryl, —(CH$_2$)$_n$—NHC(O)R⁵ and —(CH$_2$)$_n$-cycloalkyl; where n=1–4;
R² is chosen from the group consisting of alkyl, aralkyl, aryl, aryloxyalkyl, cycloalkyl, —(CH$_2$)$_n$-cycloalkyl, heteroaryl, —CH(⁶)OC(O)NHR⁵,

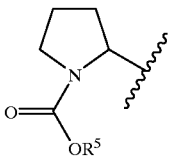 and 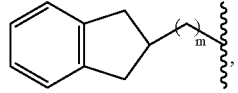

wherein m=0–3; or R² is the descarboxy residue of an N-capped-α-amino acid;
Y is —NR³R⁴ or —OR⁹;
R³ is H;
R⁴ is selected from the group consisting of heterocycloalkyl, —CH(⁵)C(O)NHR¹⁰, -benzylpyrrolidinyl-, N-benzylpiperidinyl- and —CH(R⁵)C(O)NHCH(R⁶)C(O)NHR⁷; or
R³ and R⁴ together are

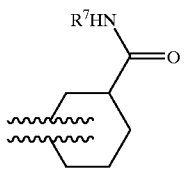 or 

R⁵ is selected from the group consisting of alkyl, aralkyl and aryl;
R⁶ is H, lower alkyl, aryl or aralkyl;
R⁷ is H or alkyl;
R⁸ is chosen from the group consisting of H, R⁵, C(O)R⁵, C(O)OR⁵ and —SO$_2$R⁵;
R⁹ is alkyl, aryl, aralkyl or R⁷CH=CH(CH$_2$)$_n$—; and
R¹⁰ is lower alkyl, aryl or aralkyl.

2. A combinatorial chemical library of claim 1 of the formula IV:

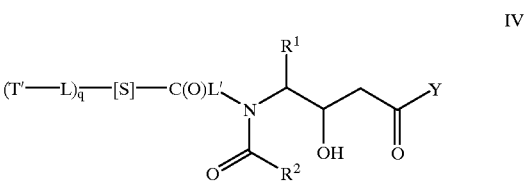

wherein:
Y is —NR³R⁴.

3. A combinatorial chemical library of claim 2 wherein:
R¹ is chosen from the group consisting of benzyl; n-butyl; isobutyl; methyl; isopropyl; 4-methoxybenzyl;

4-chlorobenzyl; 3,4-dichlorobenzyl; phenyl; phenethyl; 4-phenylbenzyl; diphenylmethyl; 1-naphthylmethyl; cyclohexylmethyl and 4-(acetamido)butyl;

$R^2$ is chosen from the group consisting of 4-chlorophenoxymethyl; isopentyl; neopentyl; cyclopentylethyl; cyclohexyl; cyclopropyl; n-pentyl; 2-furanyl; phenyl; diphenylmethyl; 4-(butoxy)phenyl; 3,4-dichlorophenyl; 3-pyridyl; 2,3-difluorophenyl; 2-fluoro-4-trifluoromethylphenyl; 2,4-dimethoxyphenyl; 3-quinolinyl; 4-phenoxyphenyl; 1-naphthyl; 4-phenylbenzyl; N-carbobenzoxy-2-pyrrolidinyl; phenylpropyl; 4(methoxyethoxy)phenethyl; 2-indanylmethyl; 3-(3,4-dimethoxyphenyl)propyl; (2,6-dimethylphenoxy)methyl; 2-naphthyloxymethyl; 2-(butylaminocarbonyloxy)-3-methylpropyl; 2-((4-phenoxyphenyl)aminocarbonyloxy)-3-methylpropyl; 2-(phenylaminocarbonyloxy)-3-methylpropyl and 2-(phenethylaminocarbonyloxy)-3-methylpropyl; and $R^4$ is selected from the group consisting of

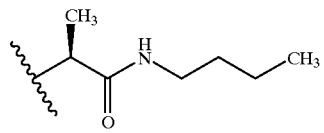

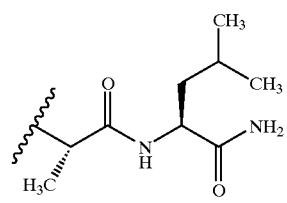

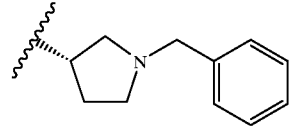

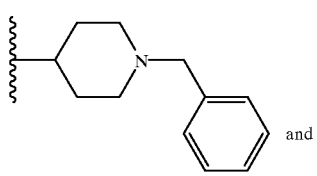

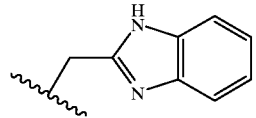

or taken together $R^3$ and $R^4$ are chosen from

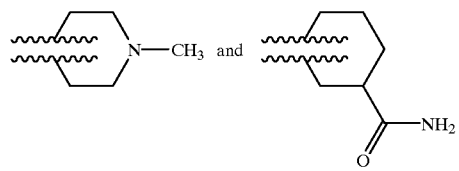

4. A combinatorial chemical library of claim 2 wherein:
$R^1$ is 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl or 4-phenylbenzyl.

5. A combinatorial chemical library of claim 2 wherein:
$R^2$ is (N-benzyloxycarbonyl)pyrrolidin-2-yl, 4-butoxyphenyl, 4-chlorophenoxymethyl, cyclohexyl, 2-cyclopentylethyl, cyclopropyl, 3,4-dichlorophenyl, 2,3-difluorophenyl, 2,4-dimethoxyphenyl, 3-(3,4-dimethoxyphenyl)propyl, 2,6-dimethylphenoxymethyl, 2,2-dimethylpropyl, 2,2-diphenylethyl, 2-fluoro-4-trifluoromethylphenyl, 2-furanyl, indan-2-ylmethyl, 4-(2-methoxy)ethoxyphenethyl, 3-methylbutyl, 1-naphthyl, 2-naphthyloxymethyl, pentyl, 4-phenoxyphenyl, phenyl, 4-(phenyl)phenyl, 3-phenylpropyl, 3-pyrrolidinyl, 3-quinolinyl or one of the following residues:

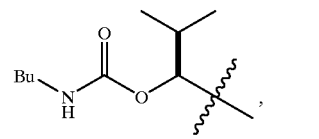

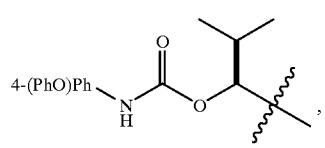

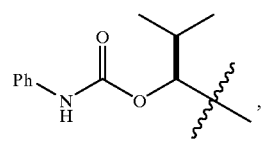

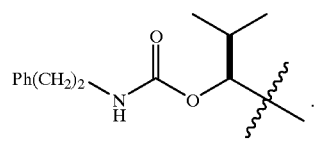

6. A combinatorial chemical library of claim 2 wherein:
$R^4$ is selected from the group consisting of 2-benzamidazolylmethyl, N-benzylpiperidin-4-yl, N-benzylpyrrolidin-3-yl, 3-imidazolylprop-1-yl,

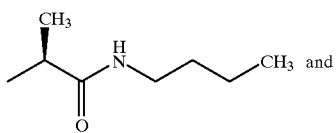

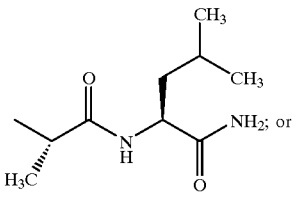

$R^3$ and $R^4$ together are 3-carboxamidopiperidinyl or 4-methylpiperazinyl.

7. A combinatorial chemical library of claim 1 wherein:

T'-L- is of the Formula II

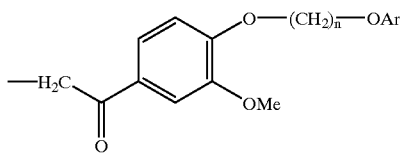

wherein:
n=3–12;
Ar is halophenyl; and
q=3–12.

8. A combinatorial chemical library of claim 7 wherein: Ar is pentachlorophenyl or 2,4,6-trichlorophenyl.

9. A combinatorial chemical library of claim 1 wherein: -L' is chosen from the group consisting of

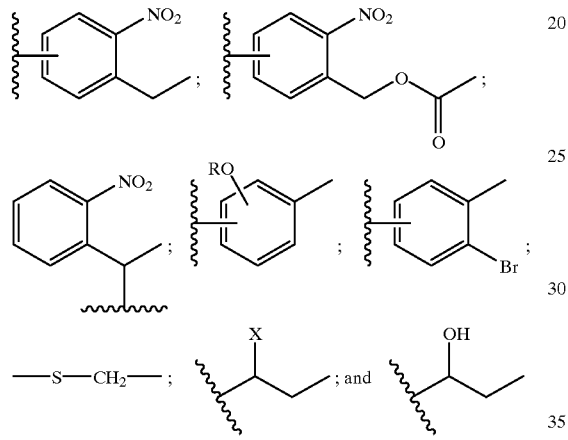

wherein X is an electron withdrawing group.

10. A combinatorial chemical library of claim 9 wherein: -L' is a photocleavable linker.

11. A combinatorial chemical library of claim 10 wherein:

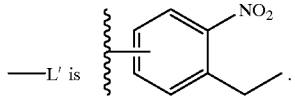

12. A combinatorial chemical library of claim 1 wherein:
q is zero; and
[S]—C(O)—L'-Z is the compound -Z attached by the linker -L' to the solid support.

13. A combinatorial chemical library of claim 1 of the formula IV:

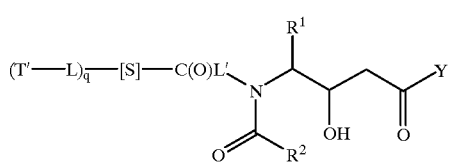

wherein:
Y is —OR$^9$.

14. A combinatorial chemical library of claim 13 wherein:
R$^1$ is chosen from the group consisting of benzyl; n-butyl; isobutyl; methyl; isopropyl; 4-methoxybenzyl; 4-chlorobenzyl; 3,4-dichlorobenzyl; phenyl; phenethyl; 4-phenylbenzyl; diphenylmethyl; 1-naphthylmethyl; cyclohexylmethyl and 4-(acetamido)butyl;

R$^2$ is chosen from the group consisting of 4-chlorophenoxymethyl; isopentyl; neopentyl; cyclopentylethyl; cyclohexyl; cyclopropyl; n-pentyl; 2-furanyl; phenyl; 4-phenylbenzyl; 4-(butoxy)phenyl; 3,4-dichlorophenyl; 3-pyridyl; 2,3-difluorophenyl; 2-fluoro-4-trifluoromethylphenyl; 2,4-dimethoxyphenyl; 3-quinolinyl; 4-phenoxyphenyl; 1-naphthyl; diphenylmethyl; -(benzyloxycarbonyl) pyrrolidin-2-yl; phenylpropyl; 4(methoxyethoxy) phenethyl; 2-indanylmethyl; 3-(3,4-dimethoxyphenyl) propyl; (2,6-dimethylphenoxy)methyl; 2-naphthyloxymethyl; 2-(butylaminocarbonyloxy)-3-methylpropyl; 2-((4-phenoxyphenyl) aminocarbonyloxy)-3-methylpropyl; 2-(phenylaminocarbonyloxy)-3-methylpropyl and 2-(phenethylaminocarbonyloxy)-3-methylpropyl; and R$^9$ is chosen from the group consisting of ethyl, allyl, benzyl, propyl and butyl.

15. A combinatorial chemical library of claim 13 wherein:
R$^1$ is 4-acetamidobutyl, benzyl, butyl, 4-chlorobenzyl, cyclohexylmethyl, 3,4-dichlorobenzyl, diphenylmethyl, isopropyl, 4-methoxybenzyl, methyl, 2-methylpropyl, 1-naphthylenemethyl, phenethyl, phenyl or 4-phenylbenzyl.

16. A combinatorial chemical library of claim 13 wherein:
R$^2$ is (N-benzyloxycarbonyl)pyrrolidin-2-yl, 4-butoxyphenyl, 4-chlorophenoxymethyl, cyclohexyl, 2-cyclopentylethyl, cyclopropyl, 3,4-dichlorophenyl, 2,3-difluorophenyl, 2,4-dimethoxyphenyl, 3-(3,4-dimethoxyphenyl)propyl, 2,6-dimethylphenoxymethyl, 2,2-dimethylpropyl, 2,2-diphenylethyl, 2-fluoro-4-trifluoromethylphenyl, 2-furanyl, indan-2-ylmethyl, 4-(2-methoxy)ethoxyphenethyl, 3-methylbutyl, 1-naphthyl, 2-naphthyloxymethyl, pentyl, 4-phenoxyphenyl, phenyl, 4-(phenyl)phenyl, 3-phenylpropyl, 3-pyrrolidinyl, 3-quinolinyl or one of the following residues:

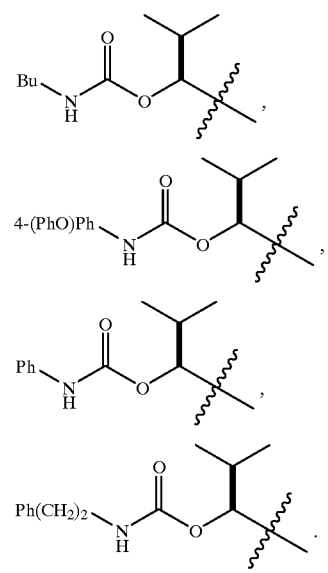

17. A combinatorial chemical library of claim 13 wherein:
R$^9$ is ethyl, allyl, propyl, butyl or benzyl.

* * * * *